US008338170B2

(12) United States Patent
Kelly et al.

(10) Patent No.: US 8,338,170 B2
(45) Date of Patent: Dec. 25, 2012

(54) METHODS FOR PURIFYING ENDODERM AND PANCREATIC ENDODERM CELLS DERIVED FROM HUMAN EMBRYONIC STEM CELLS

(75) Inventors: Olivia Kelly, San Diego, CA (US); Anne Bang, San Diego, CA (US)

(73) Assignee: Viacyte, Inc., San Diego, CA (US)

( * ) Notice: Subject to any disclaimer, the term of this patent is extended or adjusted under 35 U.S.C. 154(b) by 763 days.

(21) Appl. No.: 12/107,020

(22) Filed: Apr. 21, 2008

(65) Prior Publication Data
US 2009/0263896 A1 Oct. 22, 2009

(51) Int. Cl.
*C12N 5/00* (2006.01)
(52) U.S. Cl. ........................................ 435/325; 435/455
(58) Field of Classification Search .................. 435/325, 435/455
See application file for complete search history.

(56) References Cited

U.S. PATENT DOCUMENTS

| | | | |
|---|---|---|---|
| 2,500,388 A | 3/1950 | Simons | |
| 2,519,983 A | 8/1950 | Simons | |
| 2,594,272 A | 4/1952 | Kauck et al. | |
| 2,616,927 A | 11/1952 | Kauck et al. | |
| 4,542,104 A | 9/1985 | Stryer et al. | |
| 4,788,339 A | 11/1988 | Moore et al. | |
| 5,171,846 A | 12/1992 | Gupta | |
| 5,240,640 A | 8/1993 | Siiman et al. | |
| 5,248,772 A | 9/1993 | Siiman et al. | |
| 5,272,257 A | 12/1993 | Gupta | |
| 5,453,357 A | 9/1995 | Hogan | |
| 5,466,609 A | 11/1995 | Siiman et al. | |
| 5,527,713 A | 6/1996 | Bolton et al. | |
| 5,552,086 A | 9/1996 | Siiman et al. | |
| 5,639,620 A | 6/1997 | Siiman et al. | |
| 5,658,741 A | 8/1997 | Bolton et al. | |
| 5,670,372 A | 9/1997 | Hogan | |
| 5,690,926 A | 11/1997 | Hogan | |
| 5,707,877 A | 1/1998 | Siiman et al. | |
| 5,776,706 A | 7/1998 | Siiman et al. | |
| 5,843,780 A | 12/1998 | Thomson | |
| 5,945,293 A | 8/1999 | Siiman et al. | |
| 5,989,833 A | 11/1999 | Charon et al. | |
| 6,074,884 A | 6/2000 | Siiman et al. | |
| 6,200,806 B1 | 3/2001 | Thomson | |
| 6,251,671 B1 | 6/2001 | Hogan et al. | |
| 6,426,332 B1 | 7/2002 | Rueger et al. | |
| 7,217,569 B2 | 5/2007 | Thomson | |
| 7,247,425 B2* | 7/2007 | Messier ............................ 435/5 |
| 7,413,902 B2 | 8/2008 | Bodnar | |
| 7,432,104 B2 | 10/2008 | Mitalipova et al. | |
| 7,510,876 B2 | 3/2009 | D'Amour et al. | |
| 7,541,185 B2 | 6/2009 | D'Amour et al. | |
| 7,625,753 B2 | 12/2009 | Kelly et al. | |
| 2005/0266554 A1 | 12/2005 | D'Amour et al. | |
| 2006/0003446 A1 | 1/2006 | Keller et al. | |
| 2006/0276420 A1* | 12/2006 | Keller et al. ........................ 514/44 |
| 2007/0122905 A1 | 5/2007 | D'Amour et al. | |
| 2007/0134210 A1* | 6/2007 | Heidaran ....................... 424/93.7 |
| 2007/0154984 A1 | 7/2007 | D'Amour et al. | |
| 2007/0254359 A1 | 11/2007 | Rezania et al. | |
| 2007/0259421 A1 | 11/2007 | D'Amour et al. | |
| 2008/0009057 A1* | 1/2008 | Kubota et al. ................. 435/325 |
| 2009/0004152 A1 | 1/2009 | Martinson et al. | |
| 2009/0093372 A1 | 4/2009 | Agulnick et al. | |
| 2009/0104696 A1 | 4/2009 | Robins et al. | |
| 2009/0263896 A1 | 10/2009 | Kelly et al. | |

FOREIGN PATENT DOCUMENTS

| | | |
|---|---|---|
| EP | 0 438 520 | 7/1991 |
| WO | WO 90/07380 | 7/1990 |
| WO | WO 96/26782 | 9/1996 |
| WO | WO 2005/021728 | 3/2005 |
| WO | WO 2005/045001 | 5/2005 |
| WO | WO 2007/101130 | 9/2007 |

OTHER PUBLICATIONS

Segev, Stem Cells, 2004, vol. 22, p. 265-274.*
Ago et al., "GDF15, a cardioprotective TGF-beta superfamily protein," *Cir. Res.*, (2006) 98(3):294-7.
Asai-Coakwell et al., "GDF6, a novel locus for a spectrum of ocular developmental anomalies," *Am. J. Hum. Genet.*, (2007) 80(2):306-15.
Attisano et al., "Activation of signalling by the activin receptor complex," *Mol. Cell. Biol.*, (1996) 16(3):1066-73.
Bakre et al., "Generation of multipotential mesendodermal progenitors from mouse embryonic stem cells via sustained Wnt pathway activation," *J. Biol. Chem*, (2007) 282(43):31703-12.
Bunn et al., "Small cell lung cancer, endocrine cells of the fetal bronchus, and other neuroendocrine cells express the Leu-7 antigenic determinant present on natural killer cells," *Blood*, (1985) 65:764-768.
Buxton et al., "Growth/differentiation factor-5 (GDF-5) and skeletal development," *J. Bone Joint Surg. Am.*, (2001) 83-A Suupl. 1(Pt 1):523-30.
Caricasole et al., "Human growth-differentiation factor 3 (hGDF3): developmental regulation in human teratocarcinoma cell lines and expression in primary testicular germ cell tumours," *Oncogene*, (1998) 16(1):95-103.
Carlsson et al., "Measurements of oxygen tension in native and transplanted rat pancreatic islets," *Diabetes*, (1998), 47(7):1027-32.
Chang et al., "Genetic analysis of the mammalian transforming growth factor-beta superfamily," *Endocrine Reviews*, (2002) 23(6):787-823.
Chang et al., "Xenopus GDF6, a new antagonist of noggin and a partner of BMPs," *Development*, (1999) 126(15):3347-57.
Chen et al., "The Vg1-related protein Gdf3 acts in a Nodal signaling pathway in the pre-gastrulation mouse embryo," *Development*, (2006) 133(2):319-29.
Cheng et al., "EGF-CFC proteins are essential coreceptors for the TGF-beta signals Vg1 and GDF1," *Genes Dev.*, (2003) 17(1):31-6.
Cowan et al., "Derivation of embryonic stem-cell lines from human blastocysts," *N. Engl. J. Med.*, (2004) 350(13):1353-6.
Cunningham et al., "Growth/differentiation factor-10: a new member of the transforming growth factor-beta beta superfamily related to bone morphogenetic protein-3," *Growth Factors*, (1995) 12(2):99-109.
D'Amour et al., "Efficient differentiation of human embryonic stem cells to definitive endoderm." Nature Biotechnology, Dec. 2005, vol. 23, No. 12, pp. 1534-1541.

(Continued)

*Primary Examiner* — Michael C. Wilson

(74) *Attorney, Agent, or Firm* — Knobbe, Martens, Olson & Bear LLP

(57) ABSTRACT

The present disclosure relates to compositions and methods comprising cell surface markers for hES-derived cells, in particular, endoderm lineage cells including pancreatic endoderm-type cells, derived from hES cells.

6 Claims, 2 Drawing Sheets

OTHER PUBLICATIONS

D'Amour et al. "Production of Pancreatic Hormone-Expressing Endocrine Cells From Human Embryonic Stem Cells" (Nov. 1, 2006) Nature Biotechnology 24, 1392-1401.

Daopin et al., "Crystal structure of transforming growth factor-beta 2: an unusual fold for the superfamily," *Science*, (1992) 257(5068):369-73.

Derynck et al., "Smads: transcriptional activators of TGF-beta responses," *Cell*, (1998) 95(6):737-40.

Dionne et al., "Effect of oxygen on isolated pancreatic tissue," *ASAIO*, (1989), 35(3):739-41.

Edwards et al., "Plug flow cytometry: An automated coupling device for rapid sequential flow cytometric sample analysis," *Cytometry*, (1999) 37(2):156-9.

Gamer et al., "A novel BMP expressed in developing mouse limb, spinal cord, and tail bud is a potent mesoderm inducer in *Xenopus* embryos," *Dev. Biol.*, (1999) 208(1):222-32.

Gregorieff et al., "Wnt signaling in the intestinal epithelium: from endoderm to cancer," *Genes Dev.*, (2005) 19(8):877-90.

Hasegawa et al., "A method for the selection of human embryonic stem cell sublines with high replating efficiency after single-cell dissociation," *Stem Cells*, (2006) 24(12):2649-60.

Herpin et al., "Transforming growth factor-beta-related proteins: an ancestral and widespread superfamily of cytokines in metazoans," *Dev. Comp. Immunol.*, (2004) 461-85.

Hreinsson et al., "Growth differentiation factor-9 promotes the growth, development, and survival of human ovarian follicles in organ culture," *J. Clin. Endocrinol. Metab.*, (2002) 87(1):316-21.

Hsiao et al., "Characterization of growth-differentiation factor 15, a transforming growth factor beta superfamily member induced following liver injury," *Mol. Cell. Biol.*, (2000) 20(10):3742-51.

Johansson et al, "Tissue factor produced by the endocrine cells of the islets of langerhans is associated with a negative outcome of clinical islet transplantation," *Diabetes*, (2005) 54:1755-1762.

Kang et al., "Characterization of the distinct orthotopic bone-forming activity of 14 BMPs using recombinant adenovirus-mediated gene delivery," *Gene Ther.*, (2004) 11(17):1312-20.

Katoh et al., "Comparative integromics on BMP/GDF family," *Int. J. Mol. Med.*, (2006) 17(5):951-5.

Kelly et al., "The Wnt co-receptors Lrp5 and Lrp6 are essential for gastrulation in mice," *Development*, (2004) 131(12):2803-15.

Khalil, "TGF-beta: from latent to active," *Microbes Infect.*, (1999) 1(15):1255-63.

Köhler et al., "Continuous cultures of fused cells secreting antibody of predefined specificity," *Nature*, (1975) 256(5517) 495-7.

Kumar et al., "Nodal signaling uses activin and transforming growth factor-beta receptor-regulated Smads," *J. Biol. Chem.*, (2001) 276:656-661.

Lee, "Expression of growth/differentiation factor 1 in the nervous system: conservation of a bicistronic structure," *Proc. Natl. Acad. Sci.*, (1991) 88(10):4250-4.

Lee et al., "Regulation of myostatin activity and muscle growth," *Proc. Natl. Acad. Sci. USA*, (2001) 98(16):9306-11.

Levine et al., "GDF3 at the crossroads of TGF-beta signaling," *Cell Cycle*, (2006) 5(10):1069-73.

Ling et al., "Pituitary FSH is released by a heterodimer of the beta-subunits from the two forms of inhibin," *Nature*, (1996) 321(6072):779-82.

Lo et al., "Late-emigrating neural crest cells in the roof plate are restricted to a sensory fate by GDF7," *Proc. Natl. Acad. Sci. USA*, (2005) 102(20):7192-7.

Lopez-Coviella et al., "Bone morphogenetic protein 9 induces the transcriptome of basal forebrain cholinergic neurons," *Proc. Natl. Acad. Sci.*, (2005) 102(19):6984-9.

Maretto et al., "Mapping Wnt/beta-catenin signaling during mouse development and in colorectal tumors," *Proc. Natl. Acad. Sci. USA*, (2003) 100(6):3299-304.

Mason et al., "Complementary DNA sequences of ovarian follicular fluid inhibin show precursor structure and homology with transforming growth factor-beta," *Nature*, (1985) 318(6047):659-63.

Massagué et al., "Controlling TGF-beta signaling," *Genes Dev.*, (2000) 14(6):627-44.

Massagué et al., "How cells read TGF-beta signals," *Nat. Rev. Mol. Cell. Biol.*, (2000) 1(3):169-78.

Mathews, "Activin receptors and cellular signaling by the receptor serine kinase family," *Endocr. Rev.*, (1994) 15(3):310-25.

Mazerbourg et al., "Identification of receptors and signaling pathways for orphan bone morphogenetic protein/growth differentiation factor ligands based on genomic analyses," *J. Biol. Chem.*, (2005) 280(37):32122-32.

McLean et al. "Activin A Efficiently Specifies Definitive Endoderm from Human Embryonic Stem Cells Only When Phosphtidylinositol 3-Kinase Signaling Is Suppressed" (2007) Stem Cells 25: 29-38.

McPherron et al., "Regulation of anterior/posterior patterning of the axial skeleton by growth/differentiation factor 11," *Nat. Genet.*, (1999) 22(3):260-4.

McPherron et al., "Regulation of skeletal muscle mass in mice by a new TGF-beta superfamily member," *Nature*, (1997) 387(6628):83-90.

Nishitoh et al., "Identification of type I and type II serine/threonine kinase receptors for growth/differentiation factor-5," *J. Biol. Chem.*, (1996) 27(135):21345-52.

O'Keeffe et al., "Effects of growth/differentiation factor 5 on the survival and morphology of embryonic rat midbrain dopaminergic neurones in vitro," *J. Neurocytol.*, (2004) 33(5):479-88.

Rankin et al., "Regulation of left-right patterning in mice by growth/differentiation factor-1," *Nat. Genet.*, (2000) 24(3):262-5.

Reissmann et al., "The orphan receptor ALK7 and the Activin receptor ALK4 mediate signaling by Nodal proteins during vertebrate development," *Genes Dev.*, (2001) 15(15):2010-22.

Rice et al., "Quantitative biomarkers of stem cell differentiation based on intrinsic two-photon excited fluorescence," *J. Biomed. Opt.*, (2007) 12(6):060504.

Ring et al., "Selective glycogen synthase kinase 3 inhibitors potentiate insulin activation of glucose transport and utilization in vitro and in vivo," *Diabetes*, (2003) 52(3):588-95.

Robertson et al., "Inhibins and ovarian cancer," *Mol. Cell. Endocrinol.*, (2004) 225(1-2):65-71.

Schier et al., "Nodal signalling in vertebrate development," *Nature*, (2000) 403(6768):385-9.

Shen et al., "The EGF-CFC gene family in vertebrate development," *Trends. Genet.*, (2000) 16(7):303-9.

Siiman et al., "Immunophenotyping using gold or silver nanoparticle-polystyrene bead conjugates with multiple light scatter," *Cytometry*, (2000) 41(4):298-307.

Siiman et al., "Preparation, Microscopy, and Flow Cytometry with Excitation into Surface Plasmon Resonance Bands of Gold or Silver Nanoparticles on Aminodextran-Coated Polystyrene Beads," *J. Phys. Chem.*, (2000) 104:9795-9810.

Skinner et al., "Stimulation of Sertoli cell inhibin secretion by the testicular paracrine factor PModS," *Mol. Cell. Endocrinol.*, (1989) 66(2):239-49.

Souchelyntskyi et al., "TGF-beta signaling from a three-dimensional perspective: insight into selection of partners," *Trends Cell Biol.*, (2002) 12(7):304-7.

Stark et al., "FGFR-4, a new member of the fibroblast growth factor receptor family, expressed in the definitive endoderm and skeletal muscle lineages of the mouse," *Development*, (1991) 113:641-651.

Suscheck et al., "Primary cultures of rat islet capillary endothelial cells," *Am. J. Pathol.*, (1994) 145(3):685-695.

Truska et al., "Bone morphogenetic proteins 2, 4, and 9 stimulate murine hepcidin 1 expression independently of Hfe, transferrin receptor 2 (Tfr2), and IL-6," *Proc. Natl. Acad. Sci.*, (2006) 103(27):10283-93.

Vale et al., "Purification and characterization of an FSH releasing protein from porcine ovarian follicular fluid," *Nature*, (1986) 321(6072):776-9.

van Zonnevald et al., "Do cycle disturbances explain the age-related decline of female fertility? Cycle characteristics of women aged over 40 years compared with a reference population of young women," *Hum. Reprod.*, (2003) 18(3):495-501.

Vitt et al., "Bone morphogenetic protein receptor type II is a receptor for growth differentiation factor-9," *Biol. Reprod.*, (2002) 67(2):473-80.

Weenen et al., "Anti-Müllerian hormone expression pattern in the human ovary: potential implications for initial and cyclic follicle recruitment," *Mol. Hum. Reprod.*, (2004) 10(2):77-83.

Zhou et al., "Nodal is a novel TGF-beta-like gene expressed in the mouse node during gastrulation," *Nature*, (1993) 361:543-7.

Zimmers et al., "Growth differentiation factor-15/macrophage inhibitory cytokine-1 induction after kidney and lung injury," *Shock*, (2005) 23(6):543-8.

Zimmers et al., "Induction of cachexia in mice by systemically administered myostatin," *Science*, (2002) 296(5572):1486-8.

International Search Report and Written Opinion issued in International Application No. PCT/US2008/061053, date Mar. 27, 2009.

International Search Report and Written Opinion mailed Mar. 3, 2009 in International Application No. PCT/US2008/065686, dated Jun. 3, 2008.

Application as Filed in U.S. Appl. No. 11/993,399, filed Dec. 20, 2007.

Application as Filed in U.S. Appl. No. 12/099,759, filed Apr. 8, 2008.

\* cited by examiner

SEQUENCE LISTING

```
<160> NUMBER OF SEQ ID NOS: 59

<210> SEQ ID NO 1
<211> LENGTH: 21
<212> TYPE: DNA
<213> ORGANISM: Artificial Sequence
<220> FEATURE:
<223> OTHER INFORMATION: DNA primer

<400> SEQUENCE: 1
cagcctttgt gaaccaacac c                                              21
```

```
<210> SEQ ID NO 2
<211> LENGTH: 20
<212> TYPE: DNA
<213> ORGANISM: Artificial Sequence
<220> FEATURE:
<223> OTHER INFORMATION: DNA primer

<400> SEQUENCE: 2
cgttccccgc acactaggta                                               20

<210> SEQ ID NO 3
<211> LENGTH: 23
<212> TYPE: DNA
<213> ORGANISM: Artificial Sequence
<220> FEATURE:
<223> OTHER INFORMATION: DNA probe

<400> SEQUENCE: 3
cggctcacac ctggtggaag ctc                                           23

<210> SEQ ID NO 4
<211> LENGTH: 16
<212> TYPE: DNA
<213> ORGANISM: Artificial Sequence
<220> FEATURE:
<223> OTHER INFORMATION: DNA primer

<400> SEQUENCE: 4
ctggagggac gcacgc                                                   16

<210> SEQ ID NO 5
<211> LENGTH: 21
<212> TYPE: DNA
<213> ORGANISM: Artificial Sequence
<220> FEATURE:
<223> OTHER INFORMATION: DNA primer

<400> SEQUENCE: 5
tcccgtcttt gtccaacaaa a                                             21

<210> SEQ ID NO 6
<211> LENGTH: 26
<212> TYPE: DNA
<213> ORGANISM: Artifical Sequence
<220> FEATURE:
<223> OTHER INFORMATION: DNA probe

<400> SEQUENCE: 6
tggcctgtac ccctcatcaa ggatcc                                        26

<210> SEQ ID NO 7
<211> LENGTH: 18
<212> TYPE: DNA
<213> ORGANISM: Artificial Sequence
<220> FEATURE:
<223> OTHER INFORMATION: DNA primer

<400> SEQUENCE: 7
tggcgttgtt tgtggctg                                                 18

<210> SEQ ID NO 8
<211> LENGTH: 19
<212> TYPE: DNA
<213> ORGANISM: Artificial Sequence
<220> FEATURE:
<223> OTHER INFORMATION: DNA primer
```

```
<400> SEQUENCE: 8
aggtcccaag gtggagtgc                                            19

<210> SEQ ID NO 9
<211> LENGTH: 23
<212> TYPE: DNA
<213> ORGANISM: Artificial Sequence
<220> FEATURE:
<223> OTHER INFORMATION: DNA probe

<400> SEQUENCE: 9
tgcgcacatc cctgccctcc tac                                       23

<210> SEQ ID NO 10
<211> LENGTH: 20
<212> TYPE: DNA
<213> ORGANISM: Artificial Sequence
<220> FEATURE:
<223> OTHER INFORMATION: DNA primer

<400> SEQUENCE: 10
tctctattct tttgcgccgg                                           20

<210> SEQ ID NO 11
<211> LENGTH: 18
<212> TYPE: DNA
<213> ORGANISM: Artificial Sequence
<220> FEATURE:
<223> OTHER INFORMATION: DNA primer

<400> SEQUENCE: 11
cttggacagt gggcgcac                                             18

<210> SEQ ID NO 12
<211> LENGTH: 25
<212> TYPE: DNA
<213> ORGANISM: Artificial Sequence
<220> FEATURE:
<223> OTHER INFORMATION: DNA probe

<400> SEQUENCE: 12
agaaaggatg acgcctcaac cctcg                                     25

<210> SEQ ID NO 13
<211> LENGTH: 21
<212> TYPE: DNA
<213> ORGANISM: Artificial Sequence
<220> FEATURE:
<223> OTHER INFORMATION: DNA primer

<400> SEQUENCE: 13
ccgactggag cagctactat g                                         21

<210> SEQ ID NO 14
<211> LENGTH: 20
<212> TYPE: DNA
<213> ORGANISM: Artificial Sequence
<220> FEATURE:
<223> OTHER INFORMATION: DNA primer

<400> SEQUENCE: 14
tacgtgttca tgccgttcat                                           20

<210> SEQ ID NO 15
<211> LENGTH: 23
<212> TYPE: DNA
```

```
<213> ORGANISM: Artificial Sequence
<220> FEATURE:
<223> OTHER INFORMATION: DNA probe

<400> SEQUENCE: 15
cagagcccga gggctactcc tcc                                              23

<210> SEQ ID NO 16
<211> LENGTH: 20
<212> TYPE: DNA
<213> ORGANISM: Artificial Sequence
<220> FEATURE:
<223> OTHER INFORMATION: DNA primer

<400> SEQUENCE: 16
gctgccaagg aattcattgc                                                  20

<210> SEQ ID NO 17
<211> LENGTH: 22
<212> TYPE: DNA
<213> ORGANISM: Artificial Sequence
<220> FEATURE:
<223> OTHER INFORMATION: DNA primer

<400> SEQUENCE: 17
cttcaacaat ggcgacctct tc                                               22

<210> SEQ ID NO 18
<211> LENGTH: 24
<212> TYPE: DNA
<213> ORGANISM: Artificial Sequence
<220> FEATURE:
<223> OTHER INFORMATION: DNA probe

<400> SEQUENCE: 18
tgaaaggccg aggaaggcga gatt                                             24

<210> SEQ ID NO 19
<211> LENGTH: 20
<212> TYPE: DNA
<213> ORGANISM: Artificial Sequence
<220> FEATURE:
<223> OTHER INFORMATION: DNA primer

<400> SEQUENCE: 19
gctggggtga cctcaatcta                                                  20

<210> SEQ ID NO 20
<211> LENGTH: 20
<212> TYPE: DNA
<213> ORGANISM: Artificial Sequence
<220> FEATURE:
<223> OTHER INFORMATION: DNA primer

<400> SEQUENCE: 20
caggaacctg catgaggact                                                  20

<210> SEQ ID NO 21
<211> LENGTH: 23
<212> TYPE: DNA
<213> ORGANISM: Artificial Sequence
<220> FEATURE:
<223> OTHER INFORMATION: DNA probe

<400> SEQUENCE: 21
agtttcagag ccattgggcg gtg                                              23
```

<210> SEQ ID NO 22
<211> LENGTH: 21
<212> TYPE: DNA
<213> ORGANISM: Artificial Sequence
<220> FEATURE:
<223> OTHER INFORMATION: DNA primer

<400> SEQUENCE: 22
gagatccatg gtgttcaagg a                                              21

<210> SEQ ID NO 23
<211> LENGTH: 20
<212> TYPE: DNA
<213> ORGANISM: Artificial Sequence
<220> FEATURE:
<223> OTHER INFORMATION: DNA primer

<400> SEQUENCE: 23
gtcaaggatg cgtatggaca                                                20

<210> SEQ ID NO 24
<211> LENGTH: 23
<212> TYPE: DNA
<213> ORGANISM: Artificial Sequence
<220> FEATURE:
<223> OTHER INFORMATION: DNA probe

<400> SEQUENCE: 24
ctacattgtc cctcggcact gcc                                            23

<210> SEQ ID NO 25
<211> LENGTH: 20
<212> TYPE: DNA
<213> ORGANISM: Artificial Sequence
<220> FEATURE:
<223> OTHER INFORMATION: DNA primer

<400> SEQUENCE: 25
cagcagaatc cagacctgca                                                20

<210> SEQ ID NO 26
<211> LENGTH: 19
<212> TYPE: DNA
<213> ORGANISM: Artificial Sequence
<220> FEATURE:
<223> OTHER INFORMATION: DNA primer

<400> SEQUENCE: 26
gtcagcgcct tccacgact                                                 19

<210> SEQ ID NO 27
<211> LENGTH: 24
<212> TYPE: DNA
<213> ORGANISM: Artificial Sequence
<220> FEATURE:
<223> OTHER INFORMATION: DNA probe

<400> SEQUENCE: 27
acgccgagtt gagcaagatg ctgg                                           24

<210> SEQ ID NO 28
<211> LENGTH: 18
<212> TYPE: DNA
<213> ORGANISM: Artificial Sequence
<220> FEATURE:
<223> OTHER INFORMATION: DNA primer -continued

```
<400> SEQUENCE: 28
gccacctcgc tcatgctc                                              18

<210> SEQ ID NO 29
<211> LENGTH: 19
<212> TYPE: DNA
<213> ORGANISM: Artificial Sequence
<220> FEATURE:
<223> OTHER INFORMATION: DNA primer

<400> SEQUENCE: 29
ccatttcatc cgccggttc                                             19

<210> SEQ ID NO 30
<211> LENGTH: 26
<212> TYPE: DNA
<213> ORGANISM: Artificial Sequence
<220> FEATURE:
<223> OTHER INFORMATION: DNA probe

<400> SEQUENCE: 30
ccgagaccca gggaagattt ggttcc                                     26

<210> SEQ ID NO 31
<211> LENGTH: 19
<212> TYPE: DNA
<213> ORGANISM: Artificial Sequence
<220> FEATURE:
<223> OTHER INFORMATION: DNA primer

<400> SEQUENCE: 31
cgagggcctt cagtactcc                                             19

<210> SEQ ID NO 32
<211> LENGTH: 20
<212> TYPE: DNA
<213> ORGANISM: Artificial Sequence
<220> FEATURE:
<223> OTHER INFORMATION: DNA primer

<400> SEQUENCE: 32
ttgtcattgt ccggtgactc                                            20

<210> SEQ ID NO 33
<211> LENGTH: 23
<212> TYPE: DNA
<213> ORGANISM: Artificial Sequence
<220> FEATURE:
<223> OTHER INFORMATION: DNA probe

<400> SEQUENCE: 33
actcaagctc caagtccccg gag                                        23

<210> SEQ ID NO 34
<211> LENGTH: 21
<212> TYPE: DNA
<213> ORGANISM: Artificial Sequence
<220> FEATURE:
<223> OTHER INFORMATION: DNA primer

<400> SEQUENCE: 34
gaaggtcatc atctgccatc g                                          21

<210> SEQ ID NO 35
<211> LENGTH: 19
<212> TYPE: DNA
```

<213> ORGANISM: Artificial Sequence
<220> FEATURE:
<223> OTHER INFORMATION: DNA primer

<400> SEQUENCE: 35
ggccataatc agggtcgct                                                    19

<210> SEQ ID NO 36
<211> LENGTH: 20
<212> TYPE: DNA
<213> ORGANISM: Artificial Sequence
<220> FEATURE:
<223> OTHER INFORMATION: DNA primer

<400> SEQUENCE: 36
ccccagactc cgtcagtttc                                                   20

<210> SEQ ID NO 37
<211> LENGTH: 19
<212> TYPE: DNA
<213> ORGANISM: Artificial Sequence
<220> FEATURE:
<223> OTHER INFORMATION: DNA primer

<400> SEQUENCE: 37
tccgtctggt tgggttcag                                                    19

<210> SEQ ID NO 38
<211> LENGTH: 23
<212> TYPE: DNA
<213> ORGANISM: Artificial Sequence
<220> FEATURE:
<223> OTHER INFORMATION: DNA primer

<400> SEQUENCE: 38
ccagaaagga tgcctcataa agg                                               23

<210> SEQ ID NO 39
<211> LENGTH: 18
<212> TYPE: DNA
<213> ORGANISM: Artificial Sequence
<220> FEATURE:
<223> OTHER INFORMATION: DNA primer

<400> SEQUENCE: 39
tctgcgcgcc cctagtta                                                     18

<210> SEQ ID NO 40
<211> LENGTH: 19
<212> TYPE: DNA
<213> ORGANISM: Artificial Sequence
<220> FEATURE:
<223> OTHER INFORMATION: DNA primer

<400> SEQUENCE: 40
tgggctcgag aaggatgtg                                                    19

<210> SEQ ID NO 41
<211> LENGTH: 20
<212> TYPE: DNA
<213> ORGANISM: Artificial Sequence
<220> FEATURE:
<223> OTHER INFORMATION: DNA primer

<400> SEQUENCE: 41
gcatagtcgc tgcttgatcg                                                   20

<210> SEQ ID NO 42
<211> LENGTH: 20
<212> TYPE: DNA
<213> ORGANISM: Artificial Sequence
<220> FEATURE:
<223> OTHER INFORMATION: DNA primer

<400> SEQUENCE: 42
ccgagtccag gatccaggta                                              20

<210> SEQ ID NO 43
<211> LENGTH: 19
<212> TYPE: DNA
<213> ORGANISM: Artificial Sequence
<220> FEATURE:
<223> OTHER INFORMATION: DNA primer

<400> SEQUENCE: 43
ctctgacgcc gagacttgg                                               19

<210> SEQ ID NO 44
<211> LENGTH: 19
<212> TYPE: DNA
<213> ORGANISM: Artificial Sequence
<220> FEATURE:
<223> OTHER INFORMATION: DNA primer

<400> SEQUENCE: 44
cgggaggaag gctctcact                                               19

<210> SEQ ID NO 45
<211> LENGTH: 18
<212> TYPE: DNA
<213> ORGANISM: Artificial Sequence
<220> FEATURE:
<223> OTHER INFORMATION: DNA primer

<400> SEQUENCE: 45
gggagcggtg aagatgga                                                18

<210> SEQ ID NO 46
<211> LENGTH: 22
<212> TYPE: DNA
<213> ORGANISM: Artificial Sequence
<220> FEATURE:
<223> OTHER INFORMATION: DNA primer

<400> SEQUENCE: 46
tcatgttgct cacggaggag ta                                           22

<210> SEQ ID NO 47
<211> LENGTH: 23
<212> TYPE: DNA
<213> ORGANISM: Artificial Sequence
<220> FEATURE:
<223> OTHER INFORMATION: DNA primer

<400> SEQUENCE: 47
gaggagaaag tggaggtctg gtt                                          23

<210> SEQ ID NO 48
<211> LENGTH: 21
<212> TYPE: DNA
<213> ORGANISM: Artificial Sequence
<220> FEATURE:
<223> OTHER INFORMATION: DNA primer

```
<400> SEQUENCE: 48
ctctgatgag gaccgcttct g                                              21

<210> SEQ ID NO 49
<211> LENGTH: 21
<212> TYPE: DNA
<213> ORGANISM: Artificial Sequence
<220> FEATURE:
<223> OTHER INFORMATION: DNA primer

<400> SEQUENCE: 49
acagtgccct tcagccagac t                                              21

<210> SEQ ID NO 50
<211> LENGTH: 25
<212> TYPE: DNA
<213> ORGANISM: Artificial Sequence
<220> FEATURE:
<223> OTHER INFORMATION: DNA primer

<400> SEQUENCE: 50
acaactactt tttcacagcc ttcgt                                          25

<210> SEQ ID NO 51
<211> LENGTH: 23
<212> TYPE: DNA
<213> ORGANISM: Artificial Sequence
<220> FEATURE:
<223> OTHER INFORMATION: DNA primer

<400> SEQUENCE: 51
gagaaaccca ctggagatga aca                                            23

<210> SEQ ID NO 52
<211> LENGTH: 19
<212> TYPE: DNA
<213> ORGANISM: Artificial Sequence
<220> FEATURE:
<223> OTHER INFORMATION: DNA primer

<400> SEQUENCE: 52
atgcaccgct acgacatgg                                                 19

<210> SEQ ID NO 53
<211> LENGTH: 21
<212> TYPE: DNA
<213> ORGANISM: Artificial Sequence
<220> FEATURE:
<223> OTHER INFORMATION: DNA primer

<400> SEQUENCE: 53
ctcatgtagc cctgcgagtt g                                              21

<210> SEQ ID NO 54
<211> LENGTH: 20
<212> TYPE: DNA
<213> ORGANISM: Artificial Sequence
<220> FEATURE:
<223> OTHER INFORMATION: DNA primer

<400> SEQUENCE: 54
ctggctgtgg caaggtcttc                                                20

<210> SEQ ID NO 55
<211> LENGTH: 20
<212> TYPE: DNA
```

```
<213> ORGANISM: Artificial Sequence
<220> FEATURE:
<223> OTHER INFORMATION: DNA primer

<400> SEQUENCE: 55
cagccctcaa actcgcactt                                                    20

<210> SEQ ID NO 56
<211> LENGTH: 18
<212> TYPE: DNA
<213> ORGANISM: Artificial Sequence
<220> FEATURE:
<223> OTHER INFORMATION: DNA primer

<400> SEQUENCE: 56
atcgaggagc gccacaac                                                      18

<210> SEQ ID NO 57
<211> LENGTH: 19
<212> TYPE: DNA
<213> ORGANISM: Artificial Sequence
<220> FEATURE:
<223> OTHER INFORMATION: DNA primer

<400> SEQUENCE: 57
tgctggatgg tgtcctggt                                                     19

<210> SEQ ID NO 58
<211> LENGTH: 19
<212> TYPE: DNA
<213> ORGANISM: Artificial Sequence
<220> FEATURE:
<223> OTHER INFORMATION: DNA primer

<400> SEQUENCE: 58
cctcttgcaa tgcggaaag                                                     19

<210> SEQ ID NO 59
<211> LENGTH: 23
<212> TYPE: DNA
<213> ORGANISM: Artificial Sequence
<220> FEATURE:
<223> OTHER INFORMATION: DNA primer

<400> SEQUENCE: 59
ctcatggcaa agttcttcca gaa                                                23
```

METHODS FOR PURIFYING ENDODERM AND PANCREATIC ENDODERM CELLS DERIVED FROM HUMAN EMBRYONIC STEM CELLS

REFERENCE TO SEQUENCE LISTING

The present application is being filed along with a Sequence Listing in electronic format. The Sequence Listing is provided as a file entitled CYTHERA063A.TXT, created Apr. 21, 2008, which is 10.0 KB in size. The information in the electronic format of the Sequence Listing is incorporated herein by reference in its entirety.

FIELD OF THE INVENTION

The present invention relates to the fields of medicine and cell biology. In particular, the present invention relates to a composition comprising a human embryonic stem cell-derived pancreatic endoderm population containing at least one cell type bearing at least one cellular target or marker and a method for purifying the same.

BACKGROUND

Human embryonic stem cells (hESCs) have the potential to produce differentiated cell types comprising all human somatic tissues and organs. Cell therapy treatment of insulin dependent diabetes is facilitated by the production of unlimited numbers of pancreatic cells that can and will be able to function similarly to human islets. Accordingly, there is need for producing these pancreatic type cells derived from hES cells, as well as reliable methods for purifying such cells.

SUMMARY OF THE INVENTION

Embodiments described herein relate to methods for purifying various hES-derived cell populations.

Additional embodiments of the invention are described in the following numbered paragraphs:

1. A method of purifying a gut endoderm cell comprising: a) exposing a population of cells derived from pluripotent stem cells comprising a gut endoderm cell to a ligand which binds to a cell surface marker expressed on the gut endoderm cell, wherein said cell surface marker is selected from the group consisting of CD49e, CD99, CD165, and CD334; and b) separating the gut endoderm cell from cells derived from pluripotent stem cells which do not bind to the ligand, thereby purifying said gut endoderm cell.

2. The method of paragraph 1, wherein the ligand is an antibody or binding fragment thereof.

3. The method of paragraph 2, wherein said antibody is a monoclonal antibody.

4. The method of paragraph 2, wherein said antibody is a polyclonal antibody.

5. The method of paragraph 1, wherein the gut endoderm cell expresses at least forkhead box A2 (FOXA2).

6. A method of purifying a gut endoderm cell comprising: a) exposing a population of cells derived from pluripotent stem cells comprising a gut endoderm cell to a ligand which binds to a cell surface marker not expressed on said gut endoderm cell, wherein the cell surface marker is selected from the group consisting of CD30, CD49a and CD55; and b) separating the gut endoderm cell from cells derived from pluripotent stem cells which bind to the ligand, thereby purifying said gut endoderm cell.

7. The method of paragraph 6, wherein the gut endoderm cell expresses at least forkhead box A2 (FOXA2).

8. The method of paragraph 6, wherein the ligand is an antibody or binding fragment thereof.

9. The method of paragraph 8, wherein said antibody is a monoclonal antibody.

10. The method of paragraph 8, wherein said antibody is a polyclonal antibody.

11. A method of purifying a pancreatic endoderm cell comprising: a) exposing a population of cells derived from pluripotent stem cells comprising a pancreatic endoderm cell to a ligand which binds to a cell surface marker on the pancreatic endoderm cell, wherein the cell surface marker is selected from the group consisting of CD57 and CD142, and wherein the pancreatic endoderm cell expresses pancreatic and duodenal homeobox gene 1 (PDX1); and b) separating the pancreatic endoderm cell from cells derived from pluripotent stem cells which do not bind to the ligand, thereby purifying said pancreatic endoderm cell.

12. The method of paragraph 11, wherein the ligand is an antibody or binding fragment thereof.

13. The method of paragraph 12, wherein said antibody is a monoclonal antibody.

14. The method of paragraph 12, wherein said antibody is a polyclonal antibody.

15. The method of paragraph 11, wherein the pancreatic endoderm cell expresses NKX6.1.

16. A method of purifying a pancreatic endocrine cell comprising: a) exposing a population of cells derived from pluripotent stem cells comprising a pancreatic endocrine cell to a ligand which binds to a cell surface marker expressed on the pancreatic endocrine cell, wherein the cell surface marker is selected from the group consisting of CD57, CD200, and CD318; and b) separating the pancreatic endocrine cell from cells derived from pluripotent stem cells which do not bind to the ligand, thereby purifying said pancreatic endocrine cell.

17. The method of paragraph 16, wherein the pancreatic endocrine cell expresses at least chromogranin A (CHGA).

18. The method of paragraph 16, wherein the ligand is an antibody or binding fragment thereof.

19. The method of paragraph 18, wherein said antibody is a monoclonal antibody.

20. The method of paragraph 18, wherein said antibody is a polyclonal antibody.

21. A method of purifying a pancreatic endocrine cell comprising: a) exposing a population of cells derived from pluripotent stem cells comprising a pancreatic endocrine cell to a ligand which binds to a cell surface marker not expressed on said pancreatic endocrine cell, wherein the cell surface marker is selected from the group consisting of CD142 and CD340; and b) separating the pancreatic endocrine cell from cells derived from pluripotent stem cells which bind to the ligand, thereby purifying said pancreatic endocrine cell.

22. The method of paragraph 21 wherein the pancreatic endocrine cell expresses at least chromogranin A (CHGA).

23. The method of paragraph 21, wherein the ligand is an antibody or binding fragment thereof.

24. The method of paragraph 23, wherein said antibody is a monoclonal antibody.

25. The method of paragraph 23, wherein said antibody is a polyclonal antibody.

26. A method of purifying a pancreatic endoderm cell comprising: a) exposing a population of cells derived from pluripotent stem cells comprising a pancreatic endoderm cell to a ligand which binds to a cell surface marker not expressed on said pancreatic endoderm cell, wherein said cell surface marker is selected from the group consisting of CD55 and CD98, and wherein the pancreatic endoderm cell expresses pancreatic and duodenal homeobox gene 1 (PDX1); and b) separating the pancreatic endoderm cell from cells derived from pluripotent stem cells which bind to the ligand, thereby purifying said pancreatic endoderm cell.

27. The method of paragraph 26, wherein the ligand is an antibody or binding fragment thereof.

28. The method of paragraph 27, wherein said antibody is a monoclonal antibody.

29. The method of paragraph 27, wherein said antibody is a polyclonal antibody.

30. The method of paragraph 27, wherein the pancreatic endoderm cell expresses NKX6.1.

31. A purified cell population comprising human gut endoderm cells.

32. The purified population of paragraph 31, wherein said human gut endoderm cells comprise at least 50% of the human cells in said cell population.

33. The purified population of paragraph 31, wherein said human gut endoderm cells comprise at least 75% of the human cells in said cell population.

34. The purified population of paragraph 31, wherein said human gut endoderm cells express at least forkhead box A2 (FOXA2).

35. A purified cell population comprising human pancreatic endoderm cells.

36. The purified population of paragraph 35, wherein said human pancreatic endoderm cells comprise at least 50% of the human cells in said cell population.

37. The purified population of paragraph 35, wherein said human pancreatic endoderm cells comprise at least 75% of the human cells in said cell population.

38. The purified population of paragraph 35, wherein said human pancreatic endoderm cells express pancreatic and duodenal homeobox gene 1 (PDX1) and NKX6.1.

39. A purified cell population comprising human pancreatic endocrine cells.

40. The purified population of paragraph 39, wherein said human pancreatic endocrine cells comprise at least 50% of the human cells in said cell population.

41. The purified population of paragraph 39, wherein said human pancreatic endocrine cells comprise at least 75% of the human cells in said cell population 42. The purified population of paragraph 39, wherein said human pancreatic endocrine cells express at least chromogranin A (CHGA).

It will be appreciated that the methods and compositions described above relate to cells cultured in vitro. However, the above-described in vitro differentiated cell compositions may be used for in vivo applications.

Processes and compositions related to but distinct from the present invention can be found in U.S. Provisional Patent Application No. 60/532,004, entitled DEFINITIVE ENDODERM, filed Dec. 23, 2003; U.S. Provisional Patent Application No. 60/566,293, entitled PDX1 EXPRESSING ENDODERM, filed Apr. 27, 2004; U.S. Provisional Patent Application No. 60/586,566, entitled CHEMOKINE CELL SURFACE RECEPTOR FOR THE ISOLATION OF DEFINITIVE ENDODERM, filed Jul. 9, 2004; U.S. Provisional Patent Application No. 60/587,942, entitled CHEMOKINE CELL SURFACE RECEPTOR FOR THE ISOLATION OF DEFINITIVE ENDODERM, filed Jul. 14, 2004; U.S. patent application Ser. No. 11/021,618, entitled DEFINITIVE ENDODERM, filed Dec. 23, 2004 and U.S. patent application Ser. No. 11/115,868, entitled PDX1 EXPRESSING ENDODERM, filed Apr. 26, 2005; U.S. patent application Ser. No. 11/165,305, entitled METHODS FOR IDENTIFYING FACTORS FOR DIFFERENTIATING DEFINITIVE ENDODERM, filed Jun. 23, 2005; U.S. Provisional Patent Application No. 60/730,917, entitled PDX1-EXPRESSING DORSAL AND VENTRAL FOREGUT ENDODERM, filed Oct. 27, 2005; U.S. Provisional Patent Application No. 60/736,598, entitled MARKERS OF DEFINITIVE ENDODERM, filed Nov. 14, 2005; U.S. Provisional Patent Application No. 60/778,649, entitled INSULIN-PRODUCING CELLS AND METHOD OF PRODUCTION, filed Mar. 2, 2006; U.S. Provisional Patent Application No. 60/833,633, entitled INSULIN-PRODUCING CELLS AND METHOD OF PRODUCTION, filed Jul. 26, 2006; U.S. Provisional Patent Application No. 60/852,878, entitled ENRICHMENT OF ENDOCRINE PRECURSOR CELLS, IMMATURE PANCREATIC ISLET CELLS AND MATURE PANCREATIC ISLET CELLS USING NCAM, filed Oct. 18, 2006; U.S. patent application Ser. No. 11/588,693, entitled PDX1-EXPRESSING DORSAL AND VENTRAL FOREGUT ENDODERM, filed Oct. 27, 2006; U.S. patent application Ser. No. 11/681,687, entitled ENDOCRINE PRECURSOR CELLS, PANCREATIC HORMONE-EXPRESSING CELLS AND METHODS OF PRODUCTION, filed Mar. 2, 2007; U.S. patent application Ser. No. 11/773,944, entitled METHODS OF PRODUCING PANCREATIC HORMONES, filed Jul. 5, 2007; U.S. Patent Application No. 60/972,174, entitled METHODS OF TREATMENT FOR DIABETES, filed Sep. 13, 2007; U.S. patent application Ser. No. 11/860,494, entitled METHODS FOR INCREASING DEFINITIVE ENDODERM PRODUCTION, filed Sep. 24, 2007; and U.S. Patent Application No. 60/977,349, entitled CELL SURFACE MARKERS OF HUMAN EMBRYONIC STEM CELLS AND CANCER STEM CELLS, filed Oct. 3, 2007, the disclosures of which are incorporated herein by reference in their entireties.

DETAILED DESCRIPTION

Figure 1:
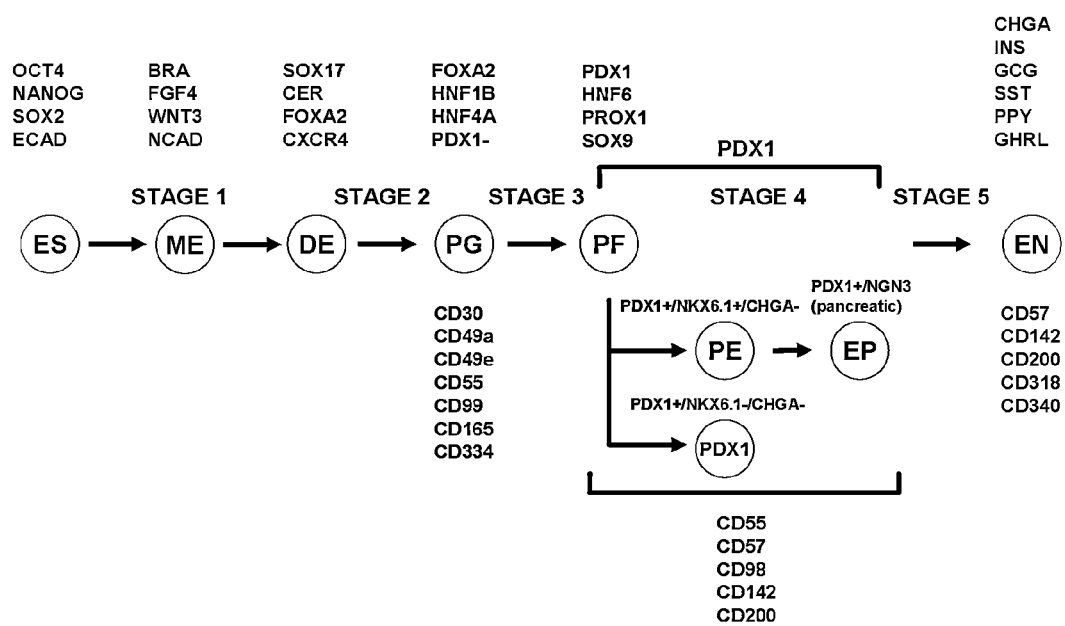
FIG. 1 is a schematic representing five-stage differentiation protocol from ES cells (ES) though mesendoderm (ME) to definitive endoderm (DE or "PDX1-negative definitive endoderm"), primitive gut tube (PG or "PDX1-negative foregut endoderm"), posterior foregut (PF or "PDX1-positive foregut endoderm), pancreatic endoderm (PE), and finally endocrine (EN) cells. The diagram also describes "signature" markers expressed in each cell type as well as selected cell surface markers that can be used to enrich or purify the indicated cell type.

Described herein are methods and compositions for identifying and characterizing various hES-derived cell types using various antibodies which cross-react to cell surface markers, receptors, membrane proteins and/or epitopes.

Also described herein is the use of hES-derived cell types, which were made from a progression of steps for converting undifferentiated hESCs to hESC-derived cells, for example, pancreatic endoderm or epithelial cells, endocrine precursor or progenitor cells, and/or hormone secreting endocrine cells. This progression of steps directs the sequential differentiation of hESCs through intermediates that are currently recognized to occur during pancreatic development in vivo. General methods for production of hESC-derived cells are described in related U.S. applications as indicated above, and d'Amour et al. 2005 *Nat. Biotechnol.* 23:1534-41, D'Amour et al. 2006 *Nat. Biotechnol.* 24(11): 1392-401 the disclosures of which are incorporated herein by reference in their entireties.

Definitions

The practice of the present invention will employ, unless otherwise indicated, conventional techniques of chemistry, molecular biology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; and E. M. Shevach and W. Strober, 1992 and periodic supplements, Current Protocols in Immunology, John Wiley & Sons, New York, N.Y., Current Protocols in Cytometry, John Wiley & Sons, New York, N.Y. Each of these general texts is herein incorporated by reference in its entirety.

It will be appreciated that the numerical ranges expressed herein include the endpoints set forth and describe all integers between the endpoints of the stated numerical range.

In some embodiments, hESCs can be derived from a "pre-implantation embryo." As used herein, "pre-implantation embryo" refers to an embryo between the stages of fertilization and implantation. Thus, a pre-implantation embryo typically has not progressed beyond the blastocyst stage. Implantation usually takes place 7-8 days after fertilization. However, implantation can take place about 2, about 3, about 4, about 5, about 6, about 7, about 8, about 9, about 10, about 11, about 12, about 13, about 14 or greater than about 14 days after fertilization.

As used herein, "multipotent" or "multipotent cell" refers to a cell type that can give rise to a limited number of other particular cell types. Multipotent cells are committed to one or more embryonic cell fates, and thus, in contrast to pluripotent cells, cannot give rise to each of the three embryonic cell lineages as well as extraembryonic cells.

In some embodiments, "pluripotent cells" are used as the starting material for pancreatic islet hormone-expressing cell differentiation. By "pluripotent" is meant that the cell can give rise to each of the three embryonic cell lineages as well as extraembryonic cells. Pluripotent cells, however, may not be capable of producing an entire organism.

In certain embodiments, the pluripotent cells used as starting material are stem cells, including human embryonic stem cells. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer.

As used herein, "human embryonic stem cells" or "hES cells" or "hESCs" or "stem cells" or "pluripotent stem cells" are cells obtained from an animal (e.g., a primate, such as a human) embryo. These terms and phrases are equivalent to the phrase, "differentiable cell". A "differentiable cell" is used to describe a cell or population of cells that can differentiate into at least partially mature cells, or that can participate in the differentiation of cells, e.g., fuse with other cells, that can differentiate into at least partially mature cells.

As used herein, the phrase, "differentiable cell" or "differentiated cell" or "hES-derived cell" can refer to pluripotent, multipotent, oligopotent or even unipotent cells, as defined in detail below. In certain embodiments, the differentiable cells are pluripotent differentiable cells. In more specific embodiments, the pluripotent differentiable cells are selected from the group consisting of embryonic stem cells, ICM/epiblast cells, primitive ectoderm cells, primordial germ cells, and teratocarcinoma cells. In one particular embodiment, the differentiable cells are mammalian embryonic stem cells. In a more particular embodiment, the differentiable cells are human embryonic stem cells. Of course, certain embodiments also contemplate differentiable cells from any source within an animal, provided the cells are differentiable as defined herein. For example, differentiable cells can be harvested from embryos, or any primordial germ layer therein, from placental or chorion tissue, or from more mature tissue such as adult stem cells including, but not limited to adipose, bone marrow, nervous tissue, mammary tissue, liver tissue, pancreas, epithelial, respiratory, gonadal and muscle tissue. In specific embodiments, the differentiable cells are embryonic stem cells. In other specific embodiments, the differentiable cells are adult stem cells. In still other specific embodiments, the stem cells are placental- or chorionic-derived stem cells.

As used herein, "partially mature cells" are cells that exhibit at least one characteristic of the phenotype, such as morphology or protein expression, of a mature cell from the same organ or tissue. Some embodiments contemplate using differentiable cells from any animal capable of generating differentiable cells, e.g., pancreatic type cells such as beta cells. The animals from which the differentiable cells are harvested can be vertebrate or invertebrate, mammalian or non-mammalian, human or non-human. Examples of animal sources include, but are not limited to, primates, rodents, canines, felines, equines, bovines and porcines.

As used herein, the term "differentiate" refers to the production of a cell type that is more differentiated than the cell type from which it is derived. The term therefore encompasses cell types that are partially and terminally differentiated. Similarly, "produced from hESCs," "derived from hESCs," "differentiated from hESCs," "h-ES derived cell" and equivalent expressions refer to the production of a differentiated cell type from hESCs in vitro and in vivo.

As used herein, "definitive endoderm" or "DE" refers to a multipotent cell that can differentiate into cells of the gut tube or organs derived from the gut tube. In accordance with certain embodiments, the definitive endoderm cells and cells derived therefrom are mammalian cells, and in a preferred embodiment, the definitive endoderm cells are human cells. In some embodiments, definitive endoderm cells express or fail to significantly express certain markers. In some embodiments, one or more markers selected from SOX17, CXCR4, MIXL1, GATA4, FOXA2, GSC, FGF17, VWF, CALCR, FOXQ1, CMKOR1, CER and CRIP1 are expressed in definitive endoderm cells. In other embodiments, one or more markers selected from OCT4, HNF4A, alpha-fetoprotein (AFP), Thrombomodulin (TM), SPARC and SOX7 are not significantly expressed in definitive endoderm cells. Definitive endoderm does not express PDX-1. See "DE" in FIG. 1.

Still other embodiments relate to cell cultures termed "PDX1-negative (PDX1-) foregut endoderm cells", "primitive gut (PG) tube endoderm cell", "gut endoderm", "foregut endoderm", or equivalents thereof. See "PG" in FIG. 1. PDX1-negative foregut endoderm cells are multipotent cells of the definitive endoderm lineage and have high SOX17, HNF4alpha (HNF4A), HNF1beta (HNF1B), FOXA1, FOXA2 expression; and low or significantly no PDX1, AFP, SOX7, SOX1, ZIC1 and NFM expression.

Other embodiments relate to cell cultures termed "PDX1-positive, dorsally-biased, foregut endoderm cells", "PDX1-positive foregut (PF) endoderm cells", "PDX1 positive endoderm", "pancreatic endoderm (PE)" or equivalents thereof. In some embodiments, the PDX1-positive foregut endoderm cells express one or more markers including PDX1, HNF6, PROX1 and SOX9. See "PF" in FIG. 1. In other embodiments, PDX1-positive foregut endoderm cells are further differentiated to other, at least, pancreatic-lineage cells, for example, PDX1-positive (PDX1+) endoderm which does not express NKX6.1 or CHGA (PDX1+/NKX6.1−/CHGA−) and PDX1-positive cells which do express NKX6.1 but do not express CHGA (PDX1+/NKX6.1+/CHGA−). See "PE" and "PDX1" cells/circles in FIG. 1. Hence, in one embodiment, a PDX1-positive foregut endoderm cell precedes a PDX1+/NKX6.1− and a PDX1+/NKX6.1+ type cell. In other aspects, PDX1+/NKX6.1− endoderm cells transition to PDX1+/NKX6.1+ endoderm cells. Both PDX1+/NKX6.1− and PDX1+/NKX6.1+ endoderm cells do not express hormone genes (e.g., insulin, glucagon, and the like); and are said to be CHGA-negative (CHGA-). However, at least a small percentage of these PDX1-positive foregut endoderm cells (PF) can further differentiate to non-pancreatic-lineage type cells, e.g., posterior stomach and duodenum.

Both PDX1-negative foregut and PDX-1 positive foregut endoderm cell populations are further described in detail in related U.S. application Ser. No. 11/588,693 entitled PDX1 EXPRESSING DORSAL AND VENTRAL FOREGUT ENDODERM, filed Oct. 27, 2006, which is herein incorporated by reference in its entirety. For example, Tables 3 and 4 of U.S. application Ser. No. 11/588,693 describes various markers in PDX1-positive foregut endoderm cells.

As described above, PDX1-positive foregut endoderm cells can further differentiate into other, at least, pancreatic-lineage type cells, e.g., PDX1+/NKX6.1+/CHGA− and/or PDX1+/NKX6.1−/CHGA− cells. In a preferred embodiment, PDX1+/NKX6.1+/CHGA− cells further differentiate to a pancreatic-lineage cell expressing PDX1 and neurogenin 3 (NGN3); and not stomach and/or duodenum NGN3-positive cells. The pancreatic-lineage NGN3-positive (NGN3+) cells can also be referred to as "endocrine progenitor (EP)", "endocrine precursor" cells. See "EP" in FIG. 1. Endocrine progenitors are multipotent cells of the definitive endoderm lineage and although they cannot differentiate into as many different cell, tissue and/or organ types as compared to less specifically differentiated definitive endoderm lineage or PDX1-positive foregut endoderm cells, they can differentiate to an endocrine or a hormone secreting cell.

Still other embodiments relate to cell cultures or populations containing "endocrine cells", "hormone secreting cells" or equivalents thereof which refer to a cell expressing one or more pancreatic hormones and is capable of has at least some of the functions of a human pancreatic islet cell. Pancreatic islet hormone-expressing cells can be mature or immature. As used herein, the term "mature" refers to a differentiated hES-derived cell, for example, an endocrine cell which is capable of secreting a hormone and is also responsive to various agents or insults which stimulates or effects the secretion of such hormone, in vitro or in vivo. For example, a mature endocrine cell as described herein is a cell which is, for example, glucose responsive. That is, in vitro or in vivo, a mature endocrine cell, e.g., a pancreatic beta cell, which is sensitive to glucose and can secrete and release insulin in a physiologically appropriate manner. As used herein, the term "immature" refers to a differentiated hES-derived cell, which in some embodiments, is not fully capable of secreting hormones, or, in other embodiments, not fully capable of secreting hormones due to various stimuli in vitro. Additionally, markers of mature and/or immature pancreatic islet hormone-expressing cells or endocrine cells include, but are not limited to, PDX1, ghrelin (GHRL), islet amyloid polypeptide (IAPP), insulin (INS), glucagon (GCG), NKX6 transcription factor related, locus 1 (NKX6.1), somatostatin (SOM; SST), pancreatic polypeptide (PP); synaptophysin (SYP), glucokinase, (GCK), Chromogranin A (CHGA) and/or connecting peptide (C-peptide). These and other markers of endocrine cells are described in related U.S. patent application Ser. No. 11/773,944 entitled METHOD FOR PRODUCING PANCREATIC HORMONES, filed Jul. 5, 2007 which is herein incorporated by reference in its entirety. The mature or immature pancreatic islet hormone-expressing cells produced by the processes described herein express one or more of the above-listed markers, thereby producing the corresponding gene products. However, it will be appreciated that mature pancreatic islet hormone-expressing cells need not express all of the above-described markers. For example, pancreatic islet hormone-expressing cells differentiated from hESCs do not co-express INS and GHRL. This pattern of gene expression is consistent with the expression of these genes in human fetal pancreas.

In certain embodiments, the terms "enriched", "isolated", "separated", "sorted", "purified" or equivalents thereof refer to a cell culture or a cell population or cell sample that contains at least about 30%, 40%, 50%, 55%, 60%, 65%, 70%, 75%, 80%, 85%, 90%, 95%, or 100% of the desired cell lineage or a desired cell having a certain cell phenotype, e.g., expressing a certain cell marker or not expressing a certain cell marker gene characteristic of that cell phenotype.

Many stem cell media culture or growth environments are embodied herein, including, but not limited to, defined media, conditioned media, feeder-free media, serum-free media and the like. As used herein, the term "growth environment" or "milieu" or equivalents thereof is an environment in which stem cells (e.g., primate embryonic stem cells) will proliferate in vitro. Features of the environment include the medium in which the cells are cultured, and a supporting structure (such as a substrate on a solid surface) if present.

As used herein, the term "enzymatically dissociated" or "enzymatically treated" or equivalents thereof refer to dissociating clusters or embryoid bodies of hES cells or hES-derived cells into single cell populations. In certain embodiments cells are dissociated to single cell preparations, e.g., cell separation by flow cytometry (FACS) and/or dispensing of live hES cells into multi-well plates for use in high throughput screening. Cowan et al., describe enzymatic dissociation of hES cells using trypsin but they are propagated as small clusters rather than single cells. See Cowan et al., New Engl. J. Med. 350:1353-1356, 2004; and Hasegawa et al., Stem Cells 24:2649-2660, 2006. In one embodiment, hES cells or hES-derived cells are enzymatically treated or dissociated using Accutase. Dissociated cells can be grown to a high density as monolayers, and still retain their pluripotency, in the case of undifferentiated hES cells. Use of Accutase is also described in PCT/US2007/62755, entitled COMPOSITIONS AND METHODS USEFUL FOR CULTURING DIFFERENTIABLE CELLS, filed Feb. 23, 2007, which is herein incorporated in its entirety by reference.

As used herein, the term "defined medium" or "defined media" or equivalents thereof refers to a biochemically defined formulation comprised solely of the biochemically-defined constituents. In some embodiments, a defined medium includes solely constituents having known chemical compositions. In other embodiments, a defined medium includes constituents that are derived from known sources. For example, a defined medium can also include factors and other compositions secreted from known tissues or cells; however, the defined medium will not include the conditioned medium from a culture of such cells. Thus, a "defined medium" can, if indicated, include particular compounds added to form the culture medium. Defined media compositions are known in the art, for example, PCT/US2007/062755 filed Jun. 13, 2007 and marketed as StemPro®hESC SFM by Invitrogen, Carlsbad, Calif., which is herein incorporated in its entirety.

As used herein, the phrase "conditioned medium" refers to a medium that is altered as compared to a base medium. For example, the conditioning of a medium can cause molecules, such as nutrients and/or growth factors, to be added to or depleted from the original levels found in the base medium. In some embodiments, a medium is conditioned by allowing cells of certain types to be grown or maintained in the medium under certain conditions for a certain period of time. For example, a medium can be conditioned by allowing hESCs to be expanded, differentiated or maintained in a medium of defined composition at a defined temperature for a defined number of hours. As will be appreciated by those of skill in the art, numerous combinations of cells, media types, durations and environmental conditions can be used to produce nearly an infinite array of conditioned media.

As used herein, the term "feeder cells" or "feeder cell layers" are cells which grow in vitro and are co-cultured with a target cell, e.g., co-cultured with stem cells. As used herein, the term "essentially free of a feeder cell" or "feeder-free" and equivalents thereof, refer to tissue culture conditions that do not contain intentionally added feeder cells. Also, a cell culture is "essentially feeder-free" when it does not contain exogenously added conditioned medium taken from a culture of feeder cells or exogenously added feeder cells. In some embodiments, "no exogenously added feeder cells" means that cells capable of developing a feeder cell layer have not been purposely introduced for that reason. Of course, if the cells to be cultured are derived from a seed culture that contained feeder cells, the incidental co-isolation and subsequent introduction into another culture of some small proportion of those feeder cells along with the desired cells (e.g., undifferentiated primate stem cells) should not be deemed as an intentional introduction of feeder cells. In such an instance, the culture contains a de minimus number of feeder cells. By "de minimus", it is meant the number or amount of feeder cells that is carried from a first culture to a second culture where the cells of the first culture have been cultured on feeder cells. Similarly, feeder cells or feeder-like cells that develop from stem cells seeded into the culture shall not be deemed to have been purposely introduced into the culture.

As used herein, the term "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knock-out-DMEM (KO-DMEM), and DMEM/F12, although any base medium that supports the growth of primate embryonic stem cells in a substantially undifferentiated state can be employed. A "basal medium" as described herein also refers to the basal medium described in PCT/US2007/062755, filed Jun. 13, 2007, which is herein incorporated in its entirety.

In some embodiments the basal medium contains "exogenous insulin or insulin substitutes", which refers to insulin or insulin substitutes that is/are not intentionally added to the compositions or methods. In other embodiments, the basal medium does not contain "exogenous insulin or insulin substitutes." Thus, in certain embodiments, the methods and compositions are free of insulin or insulin substitutes that are intentionally supplied. In other embodiments, the compositions or methods may, however, not necessarily be free of endogenous insulin. As used herein, "endogenous insulin" indicates that the cultured cells produce insulin when cultured according to the embodiments described herein. In some embodiments, endogenous insulin is used to detect residual impurities from the primary cell culture or impurities from the starting materials. In some embodiments, the compositions contain less than 5, 4, 3, 2, 1, 0.5, 0.25, 0.1 µg/ml, or 0.7 to 7 ng/ml of insulin or substantially no amounts of insulin.

Moreover, it has been demonstrated that high insulin concentration, e.g., concentrations as little as 0.2 µg/ml, is detrimental for the production of definitive endoderm cells from hES cells. See McLean et al. Stem Cells 25:29-38 2007. Contacting the cells with insulin during the TGFbeta stimulated differentiation process keeps the cells in the pluripotent undifferentiated state (Step 1 of d'Amour et al. 2006, supra). Hence, presence of high insulin can promote production of other hES-derived cells types other than definitive endoderm, which production is necessary for the further production of other endodermally-derived, hES-derived, cell types described herein. Production of hES-derived cells in a culture medium containing Knockout serum (GIBCO BRL) or Stem-Pro34 (GIBCO BRL) supplement contains about 8-16 µg/ml and 15 µg/ml of insulin respectively. See U.S. Publication 2006/0003446 to Keller et al. In contrast, hES-derived cells produced herein, in particular production of definitive endoderm cells, lack substantial amounts of insulin, e.g., the ranges described herein and in the related applications indicated above, describe production of definitive endoderm in a culture having about 0.7 ng to 7 ng/ml of insulin.

To be clear, the term "insulin" refers to the protein, or variant or fragment thereof that binds to the insulin receptor in normal physiological concentrations and can induce signaling through the insulin receptor. The term "insulin" encompasses a protein having the polypeptide sequence of native human insulin, or of other mammalian insulin, or of any homologs or variants to these sequences. Additionally, the term insulin encompasses polypeptide fragments that are capable of binding to the insulin receptor to induce signaling through the insulin receptor. The term "insulin substitute" refers to any zinc containing compound that can be used in place of insulin to give substantially similar results as insulin. Examples of insulin substitutes include, but are not limited to zinc chloride, zinc nitrate, zinc bromide, and zinc sulfate.

Additionally, insulin-like growth factors are not insulin substitutes or homologs of insulin, as contemplated in the embodiments presented herein. However, it will be appreciated that IGF-1 will inhibit definitive endoderm formation at even lower concentrations than insulin. See McLean et al. Stem Cells 25:29-38 2007. Accordingly, in another specific embodiment, the compositions and methods can comprise the use of at least one insulin-like growth factor (IGF) or a variant or a functional fragment thereof. Still, in other embodiments, the compositions and methods described herein are free of any exogenous insulin-like growth factors (IGFs). In specific embodiments, the compositions and methods described herein contain less than about 200, 150, 100, 75, 50, 25, 20, 15, 10, 9, 8, 7, 6, 5, 4, 3, 2, or 1 ng/ml of IGF-1.

The culture conditions described herein are "isotonic", which term refers to a solution having essentially the same tonicity (i.e., effective osmotic pressure equivalent) as another solution with which it is compared. In the context of cell culture, an "isotonic" medium is one in which cells can be cultured without an appreciable net flow of water across the cell membranes.

When used in connection with cell cultures and/or cell populations, the term "portion" means any non-zero amount of the cell culture or cell population, which ranges from a single cell to the entirety of the cell culture or cells population. In preferred embodiments, the term "portion" means at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94% or at least 95% of the cell culture or cell population.

With respect to cells in cell cultures or in cell populations, the term "substantially free of" or "essentially free of" means that the specified cell type of which the cell culture or cell population is free, is present in an amount of less than about 10%, less than about 9%, less than about 8%, less than about 7%, less than about 6%, less than about 5%, less than about 4%, less than about 3%, less than about 2% or less than about 1% of the total number of cells present in the cell culture or cell population.

As used herein, "marker", "epitope", "target", "receptor" or equivalents thereof can refer to any molecule that can be observed or detected. For example, a marker can include, but is not limited to, a nucleic acid, such as a transcript of a specific gene, a polypeptide product of a gene, such as a membrane protein, a non-gene product polypeptide, a glycoprotein, a carbohydrate, a glycolipid, a lipid, a lipoprotein or a small molecule (for example, molecules having a molecular weight of less than 10,000 amu). A "cell surface marker" is a marker present at the cell surface.

As used herein, "ligand" refers to a moiety or binding partner that specifically binds or cross-reacts to the marker or target or receptor or membrane protein on the cell or to the soluble analyte in a sample or solution. The target on the cell, includes but is not limited to a marker. Examples of such ligands include, but are not limited to, an antibody that binds a cellular antigen, an antibody that binds a soluble antigen, an antigen that binds an antibody already bound to the cellular or soluble antigen; a lectin that binds to a soluble carbohydrate or to a carbohydrate moiety which is a part of a glycoprotein or glycolipid; or functional fragments of such antibodies and antigens that are capable of binding; a nucleic acid sequence sufficiently complementary to a target nucleic acid sequence of the cellular target or soluble analyte to bind the target or analyte sequence, a nucleic acid sequence sufficiently complementary to a ligand nucleic acid sequence already bound to the cellular marker or target or soluble analyte, or a chemical or proteinaceous compound, such as biotin or avidin. Ligands can be soluble or can be immobilized on the capture medium (i.e., synthetically covalently linked to a bead), as indicated by the assay format, e.g., antibody affinity chromatography. As defined herein, ligands include, but are not limited to, various agents that detect and react with one or more specific cellular markers or targets or soluble analytes. Examples of ligands are those described herein which selectively bind to a target and/or epitope including, but without limitation, CD30, CD49a, CD49e, CD55, CD99, CD165, CD334, CD57, CD98, CD142, CD200, CD318, CD340 or any of the ligands and/or agents and/or antibodies which selectively bind to those targets described in Table 1 (Example 1). Further, all such ligands are characterized by the desired ability to bind the specified marker or target or analyte, whether it is soluble or bound to a cell. In one preferred embodiment, the ligand is a component that preferentially binds to all or a portion of a cell surface receptor. Thus, a ligand useful in this embodiment can be an antibody, or a fragment thereof, capable of binding to a cell surface receptor on a hES or hES-derived cell.

As used herein, the terms "contacting" or "exposing" or equivalents thereof refer to combining or mixing. For example, putative IgG, IgM, IgA, IgD, IgE or hybrids, derivatives or fragments of any of the aforementioned antibodies, can be contacted with a hES-derived cell population, including a population containing endoderm lineage cells described in Stages/Steps 1-5 of D'Amour et al. 2005 & 2006, supra and as represented in FIG. 1 as well as U.S. patent application Ser. No. 11/773,944, entitled METHODS OF PRODUCING PANCREATIC HORMONES, filed Jul. 5, 2007, the disclosure of which is incorporated herein by reference in its entirety. In some embodiments, formation of a complex between the hES-derived cell and the IgG, IgM, IgA, IgD IgE or hybrids, derivatives or fragments of any of the aforementioned antibody molecules refers to the ability of the target, receptor or membrane protein to selectively bind to the immunoglobulin molecule, or binding portion thereof, in order to form a stable complex that can be measured (i.e., detected) or quantified. Selective binding between a the target, receptor or membrane protein and an immunoglobulin molecule, or binding fragment thereof, for example, is effected under conditions suitable to form a complex; such conditions (e.g., appropriate concentrations, buffers, temperatures, reaction times) as well as methods to optimize such conditions are known to those skilled in the art, and examples are disclosed herein. Examples of complex formation conditions are also disclosed in, for example, in Sambrook et al., Molecular Cloning: A Laboratory Manual, Cold Spring Harbor Labs Press, 1989, the reference Sambrook et al., ibid., is incorporated by reference herein in its entirety.

As used herein, the term "detecting complex formation" refers to determining if any complex is formed, i.e., assaying for the presence (i.e., existence) of a complex. If complexes are formed, the amount of complexes formed can, but need not be, determined. Complex formation, or selective binding, between the target, receptor and/or membrane protein and any immunoglobulin molecule in the composition can be measured (i.e., detected, determined) using a variety of methods standard in the art (see, for example, Sambrook et al. supra), examples of which are disclosed herein.

As used herein, the term, "antibody" refers to immunoglobulin molecules and immunologically active portions of immunoglobulin (Ig) molecules, i.e., molecules that contain an antigen binding site that specifically binds (immuno reacts with) an antigen. Such antibodies or fragments include polyclonal antibodies from any native source, and native or recombinant monoclonal antibodies of classes IgG, IgM, IgA, IgD, and IgE, hybrid derivatives, and fragments of antibodies including Fab, Fab' and F(ab')2, humanized or human antibodies, recombinant or synthetic constructs containing the complementarity determining regions of an antibody, an Fc antibody fragment thereof, a single chain Fv antibody fragment, a synthetic antibody or chimeric antibody construct which shares sufficient CDRs to retain functionally equivalent binding characteristics of an antibody that binds a desired cell surface receptor, and a binding fragment produced by phage display. Certain classes have subclasses as well, such as IgG1, IgG2, and others. Furthermore, in humans, the light chain can be a kappa chain or a lambda chain. Reference herein to antibodies includes a reference to all such classes, subclasses and types of human antibody species. Antibodies used in the examples described herein were generally obtained by conventional hybridoma methods and purified from ascites fluid by ammonium sulfate (45%) precipitation, centrifugation and affinity chromatography using protein A. The standard process of making monoclonal antibodies is described in G. Kohler and C. Milstein, 1975 Nature, 256: 495-497. Of course, the particular method of making and the type of monoclonal antibody is not limited to such techniques and it is envisioned that any technique for making such antibodies is within the practice of the embodiments described herein.

Where indicated, the ligands and/or agents and/or antibodies employed in the embodiments described herein are associated with detectable labels. Hence, as used herein, the term "label" or "detectable label" refers to, for example, radioactive, fluorescent, luminescent, chemiluminescent, biological or enzymatic tags or labels of standard use in the art. Detectable labels for attachment to components useful in certain embodiments described herein can be easily selected from among numerous compositions known and readily available to one skilled in the art of diagnostic assays. In some embodiments, the label can be a small chemical molecule that is capable, acting alone, or in concert with other molecules or proteins, of providing a signal, that is detectable either directly or indirectly. In preferred embodiments, the marker or target is associated with the various ligands or competing analytes used in the assays. The reagents, ligands, competing analytes, or capture medium described herein are not limited by the particular detectable label or label system employed. In some cases, the detectable label can include the refractive index of a cell surface or bead. A detectable label can be conjugated, or otherwise bound, to nucleic acids, polypeptides, such as antibodies, or small molecules. For example, oligonucleotides described herein can be labeled subsequent to synthesis, by incorporating biotinylated dNTPs or rNTP, or some similar means (e.g., photo-cross-linking a protein derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythirin, rhodamine (Perkin Elmer Cetus), Cy2, Cy3, Cy3.5, Cy5, Cy5.5, Cy7, Fluor X (Amersham) and others, can be attached to nucleic acids. Non-limiting examples of detectable labels that can be conjugated to polypeptides such as antibodies include but are not limited to radioactive labels, such as $^{3}H$, $^{11}C$, $^{14}C$, $^{18}F$, $^{32}P$, $^{35}S$, $^{64}Cu$, $^{76}Br$, $^{86}Y$, $^{99}Tc$, $^{111}In$, $^{123}I$, $^{125}I$, or $^{177}Lu$, enzymes, such as horseradish peroxidase, fluorophores, chromophores, chemiluminescent agents, chelating complexes, dyes, colloidal gold or latex particles.

In one embodiment, particular labels enable detection by emitting a detectable signal of a particular wavelength upon excitation by a laser. Phycobiliproteins, tandem dyes, certain fluorescent proteins, small chemical molecules, and certain molecules detectable by other means can all be considered labels for flow cytometry analyses. See, e.g., the labels listed in Handbook of Fluorescent Probes and Research Chemicals, 6th Ed., R. P. Haugland, Molecular Probes, Inc., Eugene, Oreg. (1996). A ligand such as an antibody molecule, for example, directly labeled by conjugation with a biliprotein can have as many as 34 associated chromophores, each with an absorbance and quantum yield roughly comparable to those of fluorescein. Examples of biliproteins useful in the certain embodiments described herein are phycocyanin, allophycocyanin (APC), allophycocyanin B. phycoerythrin and preferably R-phycoerythrin. Phycoerythrin (PE) is among the brightest fluorescent dyes currently available.

As used herein, a "tandem dye" or equivalents thereof refers to non-naturally occurring molecules that can be formed of a biliprotein and another dye. See, for example, U.S. Pat. No. 4,542,104 and U.S. Pat. No. 5,272,257. Examples of tandem dyes useful in certain embodiments described herein are phycoerythrocyanin or PC5 (PE-Cy5, phycoerythrin-cyanin 5.1; excitation, 486-580 nm, emission, 660-680 nm) [A. S. Waggoner et al, 1993 Ann. N.Y. Acad. Sci., 677:185-193 and U.S. Pat. No. 5,171,846] and ECD (phycoerythrin-texas red; excitation, 486-575 nm, emission, 610-635 nm) [U.S. Pat. No. 4,542,104 and U.S. Pat. No. 5,272,257. Other known tandem dyes are PE-Cy5, PE-Cy7, APC-Cy5, and APC-Cy7 [M. Roederer et al, 1996 Cytometry, 24:191-197]. The biliproteins and tandem dyes are commercially available from various sources including Beckman Coulter, Inc., Miami, Fla., Molecular Probes, Inc., Eugene, Oreg. and Prozyme, Inc., San Leandro, Calif. All of these fluorescent dyes are commercially available, and their uses known to the art.

Still other labels that can be directly conjugated to the components of the certain methods described herein or used with the biliproteins or tandem dyes to add additional numbers of labeled ligands to the method include small molecules that upon excitation emit wavelengths of less than 550 nm. Hence, as used herein, a "small molecule" label or equivalents thereof refers to such molecules do not overlap with the emissions of the biliproteins. One example of such a marker is fluorescein isothiocyanate (FITC). Still other labels that can be employed in this method to provide additional colors are the proteins known as the green fluorescent proteins (GFPs) and blue fluorescent proteins (BFPs); also, in certain embodiments, labels that emit upon excitation by ultraviolet light are useful.

A detectable label can also be an enzyme that interacts with a substrate to produce the detectable signal; or a protein that is detectable by antibody binding or by binding to a suitably labeled ligand. A variety of enzyme systems operate to reveal a colorimetric signal in an assay, for example, glucose oxidase, horseradish peroxidase (HRP) or alkaline phosphatase (AP), and hexokinase in conjunction with glucose-6-phosphate dehydrogenase that reacts with ATP, glucose, and NAD+ to yield NADH that is detected as increased absorbance at 340 nm wavelength. Still additional labels such as colored latex microparticles (Bangs Laboratories, Indiana) whereby a dye is embedded and forms conjugates with an inhibitor sequence or ligand and provide a visual signal indicative of the presence of the resulting complex can be applicable for some assays described in certain embodiments. Other label systems that can be used include nanoparticles or quantum dots. Thus, any number of additional, and conventionally employed, labeling systems can be adapted to the methods described herein. One of skill in the art understands that selection and/or implementation of a label system involves only routine experimentation. The labels and markers discussed above can be obtained commercially from known sources.

As used herein, a "solid matrix" or a "solid phase capture medium" refers to any matrix or medium which allows it to be separated from the cell population sample, for example, a physiologically compatible bead. Characteristics of such a matrix or medium include refractive index, size, light scatter intensity, or carrying a fluorescent detector dye to provide a unique fluorescent signature. Such beads are conventionally available in the art. For example, one subset of solid phase capture medium includes stable colloidal particles, such as polystyrene beads ranging in size from between about 0.2 to about 5.0 microns in diameter (i.e., colloidal-sized). Such polystyrene substrates or beads can contain aldehyde and/or sulfate functional groups, such as the commercially available beads, e.g., from Interfacial Dynamics Corporation, Portland, Oreg.

As used herein, "expression" refers to the production of a material or substance as well as the level or amount of production of a material or substance. The emerging hES-derived cell populations are assessed by phenotypic markers, and expression patterns are analyzed to determine not only which factors have a positive or negative influence on the differentiation pathway, but also particular cell types. Thus, determining the expression of a specific marker refers to detecting either the relative or absolute amount of the marker that is expressed or simply detecting the presence or absence of the marker. Stated another way, if a marker is a protein, polypeptide or fragment or portion thereof, there are various methods of measuring and quantifying protein expression for the presence and abundance (levels) of one or more proteins in a particular cell or tissue. One method is to perform a Western blot against the marker/protein of interest, whereby cellular lysate is separated on a polyacrylamide gel and then probed with an antibody to the protein of interest. The antibody can either be conjugated to a fluorophore or to horseradish peroxidase for imaging or quantification. Another commonly used method for assaying the amount of a particular protein in a cell is to fuse a copy of the protein to a reporter gene such as Green fluorescent protein (GFP), which can be directly imaged using a fluorescent microscope.

In some embodiments, the phrase "does not express" and equivalents thereof refer to non-detectable expression of a marker or substance. In other embodiments, the phrase "does not express" and equivalents thereof refer to marker expression that is detectable but insignificant. In certain embodiments, insignificant marker expression refers to marker expression that is detectable by sensitive techniques, such as quantitative polymerase chain reaction, but which is not appreciably detectable by less sensitive techniques such as immunocytochemistry.

For most markers or targets described herein, the official Human Genome Organization (HUGO) gene symbol is provided. Such symbols, which are developed by the HUGO Gene Nomenclature Committee, provide unique abbreviations for each of the named human genes and gene products. These gene symbols are readily recognized and can easily be associated with a corresponding unique human gene and/or protein sequence by those of ordinary skill in the art.

In accordance with the HUGO designations, the following gene symbols are defined as follows: GHIRL—ghrelin; IAPP—islet amyloid polypeptide; INS—insulin; GCG—glucagon; ISL1—ISL1 transcription factor; PAX6—paired box gene 6; PAX4—paired box gene 4; NEUROG3—neurogenin 3 (NGN3); NKX2-2—NKX2 transcription factor related, locus 2 (NKX2.2); NKX6-1—NKX6 transcription factor related, locus 1 (NKX6.1); IPF1—insulin promoter factor 1 (PDX1); ONECUT1—one cut domain, family member 1 (HNF6); HLXB9-homeobox B9 (HB9); $TCF_2$— transcription factor 2, hepatic (HNF1b); FOXA1—forkhead box A1; HGF—hepatocyte growth factor; IGF1-insulin-like growth factor 1; POU5F1—POU domain, class 5, transcription factor 1 (OCT4); NANOG—Nanog homeobox; SOX2—SRY (sex determining region Y)-box 2; CDH1—cadherin 1, type 1, E-cadherin (ECAD); T-brachyury homolog (BRACH); FGF4-fibroblast growth factor 4; WNT3-wingless-type MMTV integration site family, member 3; SOX17—SRY (sex determining region Y)-box 17; GSC—goosecoid; CER1—(cerberus 1, cysteine knot superfamily, homolog (CER); CXCR4— chemokine (C-X-C motif) receptor 4; FGF17—fibroblast growth factor 17; FOXA2—forkhead box A2; SOX7—SRY (sex determining region Y)-box 7; SOX1-SRY (sex determining region Y)-box 1; AFP—alpha-fetoprotein; SPARC—secreted protein, acidic, cysteine-rich (osteonectin); and THBD—thrombomodulin (TM), NCAM—neural cell adhesion molecule; SYP—synaptophysin; ZIC1-Zic family member 1; NEF3—neurofilament 3 (NFM); SST—somatostatin; MAFA—v-maf musculoaponeurotic fibrosarcoma oncogene homolog A; MAFB—v-maf musculoaponeurotic fibrosarcoma oncogene homolog B; SYP—synaptophysin; CHGA—chromogranin A (parathyroid secretory protein 1).

The following provides the full gene names corresponding to non-HUGO gene symbols as well as other abbreviations that can be used herein: SS —somatostatin (SOM); PP—pancreatic polypeptide; C-peptide—connecting peptide; Ex4—exendin 4; NIC—nicotinamide and DAPT—N-[N-(3,5-difluorophenacetyl)-L-alanyl]-S-phenylglycine t-butyl ester; RA—retinoic acid; RPMI—Roswell Park Memorial Institute medium; CMRL—Connaught Medical Research Labs medium; FBS—fetal bovine serum; NBP10—NCAM binding protein 10; PTF1a—pancreas specific transcription factor 1a. The terms fibroblast growth factor 7 (FGF7) and keratinocyte growth factor (KGF) are synonymous.

The features and other details of the embodiments described herein, either as steps of certain embodiments or as combinations of parts of specific embodiments, will now be more particularly described. It will be understood that the particular embodiments described herein are shown by way of illustration and not as limitations. The principle features of this invention can be employed in various embodiments without departing from the scope of the invention.

Human Embryonic Stem Cells and hES-derived Cell Types

In some embodiments, the differentiation culture conditions and hES-derived cell types described herein are substantially similar to that described in D'Amour et al. 2006. D'Amour et al. 2006 describe a 5 step differentiation protocol which has been adapted and modified in FIG. 1: stage 1 (about 2-4 days) produces definitive endoderm (DE) from embryonic stem (ES) cells and through a mesendoderm (ME) intermediate, stage 2 (about 3 days) produces primitive gut tube (PG), stage 3 (about 3-4 days) produces posterior foregut (PF; or Pdx1-positive foregut endoderm), stage 4 (about 3-4 days) produces pancreatic endoderm (PE; or PDX11/NKX6.1 expressing cells), or pancreatic epithelium and endocrine precursor cells; and stage 5 produces hormone expressing pancreatic endocrine (EN) cells (about d15 or more). See FIG. 1 for a schematic representation of the 5 stage differentiation protocol. FIG. 1 also describes various markers typical or which characterizes the indicated cell type. Additional embodiments of differentiation culture conditions and hES-derived cell types described herein can be found in U.S. patent application Ser. No. 11/773,944, entitled METHODS OF PRODUCING PANCREATIC HORMONES, filed Jul. 5, 2007, the disclosure of which is incorporated herein by reference in its entirety.

A preferred embodiment for deriving these hES-derived cell types utilizes human embryonic stem cells as the starting material. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein by reference in their entireties.

In some embodiments, hESCs are maintained on a feeder layer or can be maintained feed-free. In such processes where a feeder layer is employed, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs. See U.S. patent application Ser. No. 10/486,408 entitled ALTERNATIVE COMPOSITIONS & METHODS FOR THE CULTURE OF STEM CELLS, filed Feb. 6, 2004, the disclosure of which is incorporated herein by reference in its entirety. Alternative processes permit the maintenance of pluripotent HESC without the use of a feeder layer. Methods of maintaining pluripotent hESCs under feeder-free conditions have been described in U.S. Patent Application No. 2003/0175956 and U.S. patent application Ser. No. 11/875,057, entitled METHODS AND COMPOSITIONS FOR FEEDER FREE PLURIPOTENT STEM CELL MEDIA CONTAINING HUMAN SERUM, filed Oct. 19, 2007, the disclosures of which are incorporated herein by reference in their entirety.

The human embryonic stem cells used herein can be maintained in culture either with or without serum ("serum-free"). In some embryonic stem cell maintenance procedures, serum replacement is used. In others, serum free culture techniques, such as those described in U.S. Patent Application No. 2003/0190748, the disclosure of which is incorporated herein by reference in its entirety, are used.

In some embodiments, stem cells are maintained in culture in a pluripotent state by routine passage until it is desired that they be differentiated into lineages of the three germ layers, including endodermal lineages, further including definitive endoderm, foregut endoderm, PDX1 foregut endoderm, pancreatic epithelium, endocrine precursor cells and/or pancreatic islet hormone-expressing or endocrine cells. Method of differentiating pluripotent hESCs to these cells types are described in related applications as indicated above, which are herein incorporated in their entirety; and substantially as described in d'Amour et al. 2005 and 2006, supra.

Monitoring of hES-Derived Cells

The progression of the hES-derived cells described herein (e.g., cells produced as a result of Stages or Steps 1-5 as described in d'Amour et al. 2006, supra, can be monitored by determining the expression of markers characteristic of each hES-derived cell type along the developmental pathway. In some embodiments, the identification and characterization of a hES-derived cell type is by expression of a certain marker or different expression levels and patterns of more than one marker. Specifically, the presence or absence, the high or low expression, of one or more the marker(s) can typify and identify a cell-type. Also, certain markers can have transient expression, whereby the marker is highly expressed during one stage of development and poorly expressed in another stage of development. The expression of certain markers can be determined by measuring the level at which the marker is present in the cells of the cell culture or cell population as compared to a standardized or normalized control marker. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest (e.g., e.g. Western blot, flow cytometry analysis, and the like). In certain processes, the expression of marker genes characteristic of hES-derived cells as well as the lack of significant expression of marker genes characteristic of hES-derived cells. Still further methods for characterizing and identifying hES-derived cells types is described in related applications as indicated above, which is herein incorporated in its entirety.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for particular markers listed in this disclosure can be obtained from public databases such as GenBank.

The choice of primers for use in nucleic acid amplification will depend on the marker or target nucleic acid sequence. Primers used in preferred embodiments are generally oligonucleotides, usually deoxyribonucleotides several nucleotides in length, that can be extended in a template-specific manner by the polymerase chain reaction. The design of suitable primers for amplifying a marker or target nucleic acid is within the skill of practitioners in the art. In general, the following factors are considered in primer design: a) each individual primer of a pair preferably does not self-hybridize; b) the individual pairs preferably do not cross-hybridize; and c) the selected pair must have the appropriate length and sequence homology in order to anneal to two distinct regions flanking the nucleic acid segment to be amplified. However, not every nucleotide of the primer must anneal to the template for extension to occur. The primer sequence need not reflect the exact sequence of the marker or target nucleic acid. For example, a non-complementary nucleotide fragment can be attached to the 5' end of the primer with the remainder of the primer sequence being complementary to the target. Alternatively, non-complementary bases can be interspersed into the primer, provided that the primer sequence has sufficient complementarily with the target for annealing to occur and allow synthesis of a complementary nucleic acid strand.

For a convenient detection of the amplified nucleotide acids resulting from PCR or any other nucleic acid amplification reactions described above or known in the art, primers can be conjugated to a detectable label. Detectable labels suitable for use include, but are not limited to, any composition detectable by spectroscopic, photochemical, biochemical, immunochemical, electrical, optical or chemical means. A wide variety of appropriate detectable labels are known in the art, which include luminescent labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

Amplification probe/primer combinations suitable for use in amplification assays include the following: Insulin (GenBank NM_000207): primers CAGCCTTTGTGAACCAACACC (SEQ ID NO: 1); CGTTCCCCGCACACTAGGTA (SEQ ID NO: 2); probe CGGCTCACACCTGGTGGAAGCTC (SEQ ID NO: 3). Nkx6.1 (NM_006168): primers CTGGAGGGACGCACGC (SEQ ID NO: 4); TCCCGTCTTTGTCCAACAAAA (SEQ ID NO: 5); probe TGGCCTGTACCCCTCATCAAGGATCC (SEQ ID NO: 6). Pdx1 (NM_000209): primers TGGCGTTGTTTGTGGCTG (SEQ ID NO: 7); AGGTCCCAAGGTGGAGTGC (SEQ ID NO: 8); probe TGCGCACATCCCTGCCCTCCTAC (SEQ ID NO: 9). Ngn3 (NM_020999): primers TCTCTATTCTTTTGCGCCGG (SEQ ID NO: 10); CTTGGACAGTGGGCGCAC (SEQ ID NO: 11); probe AGAAAGGATGACGCCTCAACCCTCG (SEQ ID NO: 12). HNF3B (NM_021784): primers CCGACTGGAGCAGCTACTATG (SEQ ID NO: 13); TACGTGTTCATGCCGTTCAT (SEQ ID NO: 14); probe CAGAGCCCGAGGGCTACTCCTCC (SEQ ID NO: 15); glucagon (NM_002054): primers GCTGCCAAGGAATTCATTGC (SEQ ID NO: 16); CTTCAACAATGGCGACCTCTTC (SEQ ID NO: 17); probe TGAAAGGCCGAGGAAGGCGAGATT (SEQ ID NO: 18). HNF6 (NM_030712): primers GCTGGGGTGACCTCAATCTA (SEQ ID NO: 19); CAGGAACCTGCATGAGGACT (SEQ ID NO: 20); probe AGTTTCAGAGCCATTGGGCGGTG (SEQ ID NO: 21); HNF4A (NM 000457): primers GAGATCCATGGTGTTCAAGGA (SEQ ID NO: 22); GTCAAGGATGCGTATGGACA (SEQ ID NO: 23); probe CTACATTGTCCCTCGGCACTGCC (SEQ ID NO: 24). Sox17 (NM_022454): primers CAGCAGAATCCAGACCTGCA (SEQ ID NO: 25); GTCAGCGCCTTCCACGACT (SEQ ID NO: 26); probe ACGCCGAGTTGAGCAAGATGCTGG (SEQ ID NO: 27). HIxb9 (NM_005515): primers GCCACCTCGCTCATGCTC (SEQ ID NO: 28); CCATTTCATCCGCCGGTTC (SEQ ID NO: 29); probe CCGAGACCCAGGGAAGATTTGGTTCC (SEQ ID NO: 30). Nkx2.2 (NM_002509): primers CGAGGGCCTTCAGTACTCC (SEQ ID NO: 31); TTGTCATTGTCCGGTGACTC (SEQ ID NO: 32); probe ACTCAAGCTCCAAGTCCCCGGAG (SEQ ID NO: 33). PTF1a (NM_178161): primers GAAGGTCATCATCTGCCATCG (SEQ ID NO: 34) GGCCATAATCAGGGTCGCT (SEQ ID NO: 35). SST (NM_001048): primers CCCCAGACTCCGTCAGTTTC (SEQ ID NO: 36); TCCGTCTGGTTGGGTTCAG (SEQ ID NO: 37); and PAX6 (NM_000280): primers CCAGAAAGGATGCCTCATAAAGG (SEQ ID NO: 38); TCTGCGCGCCCCTAGTTA (SEQ ID NO: 39). Oct4 primers: TGGGCTCGAGAAGGATGTG (SEQ ID NO: 40) GCATAGTCGCTGCTTGATCG (SEQ ID NO: 41). MIXL1 primers CCGAGTCCAGGATCCAGGTA (SEQ ID NO: 42) CTCTGACGCCGAGACTTGG (SEQ ID NO: 43). GATA4 primers CCTCTTGCAATGCGGAAAG (SEQ ID NO: 58) CGGGAGGAAGGCTCTCACT (SEQ ID NO: 44). FOXA2 primers GGGAGCGGTGAAGATGGA (SEQ ID NO: 45) TCATGTTGCTCACGGAGGAGTA (SEQ ID NO: 46). GSC primers GAGGAGAAAGTGGAGGTCTGGTT (SEQ ID NO: 47) CTCTGATGAGGACCGCTTCTG (SEQ ID NO: 48). CER primers ACAGTGCCCTTCAGCCAGACT (SEQ ID NO: 49) ACAACTACTTTTTCACAGCCTTCGT (SEQ ID NO: 50). AFP primers GAGAAACCCACTGGAGATGAACA (SEQ ID NO: 51) CTCATGGCAAAGTTCTTCCAGAA (SEQ ID NO: 59). SOX1 primers ATGCACCGCTACGACATGG (SEQ ID NO: 52) CTCATGTAGCCCTGCGAGTTG (SEQ ID NO: 53). ZIC1 primers CTGGCTGTGGCAAGGTCTTC (SEQ ID NO: 54) CAGCCCTCAAACTCGCACTT (SEQ ID NO: 55). NFM primers ATCGAGGAGCGCCACAAC (SEQ ID NO: 56) TGCTGGATGGTGTCCTGGT (SEQ ID NO: 57). Other primers are available though ABI Taqman including FGF17 (Hs00182599 ml), VWF (Hs00169795 ml), CMKOR1 (Hs00604567 ml), CRIP1 (Hs00832816_g1), FOXQ1 (Hs00536425_s1), CALCR (Hs00156229_m1) and CHGA (Hs00154441 ml).

In other embodiments, the expression levels of any marker in hES-derived cell types or hES-derived cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher as compared to a standardized or normalized control marker.

Purification of hES-Derived Cells

With respect to additional aspects of the embodiments described herein, the hES-derived cell types described herein can be enriched, depleted, isolated, separated, sorted and/or purified as further described in the examples. As used herein, the terms "enriched" or "purified" or enriched or purified due to depletion of other known cell populations, indicate that the cell population has been subject to some selection process so that the population is enriched and/or purified. Also, the subject cells are also considered relatively enriched and/or purified, i.e. there is significantly more of a particular hES-derived cell type population as compared to another hES-derived type population, or as compared to pluripotent undifferentiated hES cells before "enrichment" or "purification", or as compared to the original or initial cell culture. That said, sometimes enriching or purifying for particular hES-derived cells types can involve "depleting" or "separating" or "sorting" one or more known hES-derived cell type from another hES-derived cell type. For example, in some embodiments, certain hES-derived cell types are enriched or purified because they do not bind or cross-react to a ligand and/or agent and/or antibody and/or antibody bound to solid or semi-solid matrix. Such enriched or purified populations can be said to be "depleted" or "separated" or "sorted" from the hES cell culture. As a further example, such depleted or separated or sorted hES-cell populations can be found or isolated in the flow-through fractions in a standard affinity chromatography method; or stated in another way, the nonbinding fractions. Accordingly, in certain embodiments, it is advantageous to enrich and purify an hES-derived cell type by depleting the culture of known or unknown cell types. In this way, the enriched or purified cell population does not have the bound or attached antibody. Because there is no need to remove the antibody from the purified population, the use of the enriched or purified cells for cell therapies is improved.

The hES-derived cells of the present invention can be produced by employing methods described in the related application as indicated above. For example, methods of expanding definitive endoderm is described in U.S. patent application Ser. No. 11/317,387, entitled EXPANSION OF DEFINITIVE ENDODERM, filed Dec. 22, 2005; U.S. patent application Ser. No. 11/860,494, entitled METHODS FOR INCREASING DEFINITIVE ENDODERM PRODUCTION, filed Sep. 24, 2007; U.S. patent application Ser. No. 11/588,693, entitled PDX1-EXPRESSING DORSAL AND VENTRAL FOREGUT ENDODERM, filed Oct. 27, 2006; U.S. patent application Ser. No. 11/681,687, entitled ENDOCRINE PRECURSOR CELLS, PANCREATIC HORMONE EXPRESSING CELLS AND METHODS OF PRODUCTION, filed Mar. 2, 2007; U.S. patent application Ser. No. 11/773,944 entitled METHODS FOR PRODUCING PANCREATIC HORMONES, filed Jul. 5, 2007; and U.S. patent application Ser. No. 11/860,494 entitled METHODS OF INCREASING DEFINITIVE ENDODERM, filed Sep. 24, 2007, which are herein incorporated in their entirety. One method described herein and in d'Amour et al. 2005 and 2006, supra, is directed differentiation of a pluripotent stem cell to different hES-derived cell types, e.g., definitive endoderm and insulin secreting type cells.

Human ES-derived cells described herein can be enriched, depleted, isolated, separated, sorted and/or purified by using an affinity tag that is specific for such cells, e.g., an antibody. Examples of affinity tags specific for hESCs or hES-derived cells are polyclonal and/or monoclonal antibodies, antibody binding fragments, ligands or other binding agents that are specific to a marker molecule, such as a polypeptide, that is present on the cell surface of hES-derived cell or pluripotent hESC, but which is not substantially present on other cell types that would be found in a cell culture produced by the methods described herein.

Embodiments for enriching, depleting, isolating, separating, sorting and/or purifying include those described herein such as, antibody-coated magnetic beads, affinity chromatography and "panning" with antibody attached to a solid matrix or solid phase capture medium, e.g. plate, column or other convenient and available technique. Techniques providing accurate separation include flow cytometry methods which are useful for measuring cell surface and intracellular parameters, as well as shape change and granularity and for analyses of beads used as antibody- or probe-linked reagents. Readouts from flow cytometry assays include, but are not limited to, the mean fluorescence associated with individual fluorescent antibody-detected cell surface molecules or cytokines, or the average fluorescence intensity, the median fluorescence intensity, the variance in fluorescence intensity, or some relationship among these. In some aspects of embodiments with analytical steps involving flow cytometry, minimal parameters or characteristics of the beads are scatter (FS and/or SS) and at least one fluorescent wavelengths. Flow cytometry can be used to quantitate parameters such as the presence of cell surface proteins or conformational or posttranslational modification thereof, intracellular or secreted protein, where permeabilization allows antibody (or probe) access, and the like. Flow cytometry methods are known in the art, and described in the following: Flow Cytometry and Cell Storing (Springer Lab Manual), Radbruch, Ed., Springer Verlag, 2000; Ormerod, Flow Cytometry, Springer Verlag, 1999; Flow Cytometry Protocols (Methods in Molecular Biology, No 91), Jaroszeski and Heller, Eds., Humana Press, 1998; Current Protocols in Cytometry, Robinson et al., eds, John Wiley & Sons, New York, N.Y., 2000.

Also, the staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining can differ with a particular fluorochrome and reagent preparation, the data can be normalized to a control. In order to normalize the distribution to a control, each cell is recorded as a data point having a particular intensity of staining. These data points can be displayed according to a log scale, where the unit of measure is arbitrary staining intensity. In one example, the brightest cells in a population are designated as 4 logs more intense than the cells having the lowest level of staining. When displayed in this manner, it is clear that the cells falling in the highest log of staining intensity are bright or high, while those in the lowest intensity are negative. The "low" staining cells, which fall in the 2-3 log of staining intensity, can have properties that are unique from the negative and positive cells. In an alternative embodiment, the control utilizes a substrate having a defined density of marker on its surface, for example a fabricated bead or cell line, which provides the positive control for intensity. The "low" designation indicates that the level of staining is above the brightness of an isotype matched control, but is not as intense as the most brightly staining cells normally found in the population. The readouts of selected parameters are capable of being read simultaneously, or in sequence during a single analysis, as for example through the use of fluorescent antibodies to cell surface molecules. As an example, these can be tagged with different fluorochromes, fluorescent bead, tags, e.g. quantum dots, etc., allowing analysis of up to 4 or more fluorescent colors simultaneously by flow cytometry. For example, a negative designation indicates that the level of staining is at or below the brightness of an isotype matched negative control; whereas a dim designation indicates that the level of staining can be near the level of a negative stain, but can also be brighter than an isotype matched control.

Identifiers of individual cells, for example different cell types or cell type variants, can be fluorescent, as for example labeling of different unit cell types with different levels of a fluorescent compound, and the like as described herein above. In some aspects of embodiments where two cell types are to be mixed, one is labeled and the other not. In some aspects of embodiments where three or more cell types are to be included, each cell type is labeled to different levels of fluorescence by incubation with different concentrations of a labeling compound, or for different times. As identifiers of large numbers of cells, a matrix of fluorescence labeling intensities of two or more different fluorescent colors can be used, such that the number of distinct unit cell types that are identified is a number of fluorescent levels of one color, e.g., carboxyfluorescein succinimidyl ester (CFSE), times the number of fluorescence levels employed of the second color, e.g. tetramethylrhodamine isothiocyanate (TRITC), or the like, times the number of levels of a third color, etc. Alternatively, intrinsic light scattering properties of the different cell types, or characteristics of the BioMAPs of the test parameters included in the analysis, can be used in addition to or in place of fluorescent labels as unit cell type identifiers.

Still, other techniques for enriching, depleting, separating, sorting and/or purifying include plug-flow flow cytometry which has the potential to automate the delivery of small samples from unpressurized sources at rates compatible with many screening and assay applications, and can allow higher throughput, compatible with high throughput screening, Edwards et al. (1999) Cytometry 37:156-9. Also, both single cell multi-parameter and multicell multi-parameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999. For example, an alternative technique allows for staining of dead cells which can be eliminated by selection with dyes such as propidium iodide. However, any technique can be employed which is not unduly detrimental to the viability of the selected cells.

In another aspect, hES-derived cells can be enriched, depleted, separated, sorted and/or purified using conventional affinity or antibody techniques. For example, the ligand and/or antibody can be conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses can be employed with the FACS or in a combination of immuno-magnetic separation and flow cytometry. In some embodiments, multi-color analysis is of interest for the separation of cells based on multiple surface antigens. Fluorochro which find use in a multi-color analysis include, but are not limited to, phycobiliproteins, e.g. phycoerythrin and allophycocyanins; fluorescein and Texas red as described herein.

In one embodiment, the ligand, agent, and/or antibodies described herein are directly or indirectly conjugated to a magnetic reagent, such as a super-paramagnetic microparticle (microparticle). Direct conjugation to a magnetic particle is achieved by use of various chemical linking groups, as known in the art. In some embodiments, the antibody is coupled to the microparticles through side chain amino or sufhydryl groups and heterofunctional cross-linking reagents. A large number of heterofunctional compounds are available for linking to entities. For example, at least, 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle can be used. An example of a magnetic separation device is described in WO 90/07380, PCT/US96/00953, and EP 438,520, incorporated herein by reference in its entirety. The purified cell population can be collected in any appropriate medium.

In other embodiments, antibodies are indirectly coupled to the magnetic particles, e.g., the antibody is directly conjugated to a hapten, and hapten-specific second stage antibodies are conjugated to the particles. Suitable haptens include, but are not limited to, digoxin, digoxigenin, FITC, dinitrophenyl, nitrophenyl, avidin, biotin, etc. Methods for conjugation of the hapten to a protein are known in the art, and kits for such conjugations are commercially available.

In other embodiments, the antibody is coupled to a solid matrix or capture medium and added to a cell sample. For example, a capture medium includes a polystyrene bead, or a polystyrene bead which has an aminodextran coating over its peripheral surface and/or a colloidal-metal coating. Preferably an aminodextran coating is covalently bonded to the core substrate by covalent bonds between the free amino groups of the aminodextran and the amine-reactive functional groups of the polystyrene substrate and further by cross-linking with an agent such as glutaraldehyde. A variety of aminodextran beads are described in U.S. Pat. Nos. 6,074,884; 5,945,293; and 5,658,741. Aminodextran-coated monodispersed colloidal dispersions of magnetic ferrite [U.S. Pat. No. 5,240,640], metal [U.S. Pat. No. 5,248,772], polystyrene [U.S. Pat. No. 5,466,609; U.S. Pat. No. 5,707,877; U.S. Pat. No. 5,639,620; U.S. Pat. No. 5,776,706], and polystyrene-metal [U.S. Pat. No. 5,552,086; U.S. Pat. No. 5,527,713] particles can also be employed as formed bodies according to particular embodiments described herein. The disclosures of these patents are herein incorporated by reference in their entirety.

In other embodiments, another type of bead contains the above-described coated substrate with a layer of colloidal-sized metallic solid overlaying the aminodextran coating. Preferably this layer is uniformly dispersed over the dispersed surface of the aminodextran layer. The colloidal metal useful in forming the coated substrate is generally described as a metal which can be reduced from the ionic state to the metal (0) state by the aminodextran coating, or a metal which can form metal ions or metal ion complexes which have a reduction potential of about +0.7 volts or higher. In certain embodiments the metal ions employed include: Ag(I), Au(III), Pd(II), Pt(II), Rh(III), Ir(III), Ru(II), and Os(II). In a preferred embodiment, metal ions for such use are colloidal gold(III) and colloidal silver(I). Specifically, gold/silver colloid coated polystyrene-aminodextran beads, their preparation, characterization and use in analyses of subpopulations of white blood cells in whole blood have been described. See, e.g., U.S. Pat. No. 5,248,772; U.S. Pat. No. 5,552,086; U.S. Pat. Nos. 5,945,293; and O, Siiman and A. Burshteyn, 2000 J. Phys. Chem., 104:9795-9810; and O, Siiman et al, 2000 Cytometry, 41:298-307, the disclosure of which is herein incorporated by reference in its entirety. Still, an alternative to this coated bead employs carboxy-functionalized polystyrene particles as the core substrate, coated with aminodextran by EDAC coupling as described in U.S. Pat. No. 5,639,620, the disclosure of which is herein incorporated by reference in its entirety.

The capture medium can have bound thereto multiple ligands or multiple competing analytes. Each ligand bound to the capture medium is capable of binding to a soluble analyte or binding to an antibody that is itself capable of binding to the soluble analyte. Each competing analyte bound to the capture medium is capable of binding to a ligand (e.g., an antibody) that is capable of binding to the soluble analyte (whether labeled or unlabeled). Such ligands or competing analytes are associated or immobilized on the capture medium by conventional methods. For example, ligands or analytes such as antibodies, antigens, or linkers (e.g. Streptavidin, Protein A) can be attached to beads depending upon format of the analyte assay (competitive, immune-complex or sandwich) as described below. The beads can also be associated with detectable labels, preferably fluorescent labels, such as discussed above.

Beads can be fluorescent or non-fluorescent, can be of different sizes or different fluorescent intensities, or both, for differentiation of multiple analytes. If using fluorescent intensity for labeling beads, it is preferred that the fluorescence emission should be unique for each population directed to a different analyte. Bead populations of different intensity are preferably resolvable if fluorescence of the bead is used as the only detectable label for discriminating among the soluble analyte and cellular target. Alternatively, if the size of the bead populations is used as the sole detectable label for discrimination among the soluble analyte and cellular target, each bead population must have a different forward scatter (FS) or side scatter (SS) than the cell population of interest in the assay.

In one embodiment the bead is from 0.05 to 20 microns in diameter. In another embodiment, the bead is from 5 to 7 microns. In still another embodiment, the capture medium is greater than 1 μM in size. Mixtures of a variety of sizes of beads can also be employed, particularly where there are more than one soluble analyte to be detected. Generally, bead size impacts the sensitivity range of the assay, because smaller beads bind less antibody. Therefore, in one embodiment, in which high sensitivity is required, a smaller number of larger beads is desirable for the assays. In the presence of large numbers of soluble analytes, a higher number of beads (both large and small) can be employed in these methods. For use in some embodiments of, the capture medium or bead is larger than the soluble analyte to be detected. The relative volumes of the bead used in the sample container of the methods described herein are dependent upon bead concentration, analyte detection limits, and the cellular marker or target, and sample size.

In preferred embodiments, the antibody is capable of binding to at least one marker or target on a cell. The amount of the antibody necessary to bind a particular cell subset is empirically determined by performing a test separation and analysis. The cells and antibody are incubated for a period of time sufficient for complexes to form, usually at least about 5 min, more usually at least about 10 min, and usually not more than thirty (30) minutes to one hour; time can also be a variable of the incubation temperature.

In still another embodiment, hES-derived cells can be enriched, depleted, separated, sorted, isolated and/or purified using techniques for sample purification employing aspects of typical immunity complex assays. In an aspect of this embodiment, a sample, such as a sample of an hES-derived cell population, is introduced into a container, such as any tissue culture container. A known concentration of a first soluble ligand capable of binding to a single cellular target is added to the sample. This first ligand is desirably associated with a first detectable label. Multiple of the first ligands may bind to the cell. For example, a known concentration of a first soluble antibody, which is capable of binding to a single cellular target, is added to a hES-derived cell population in a tissue culture container. After incubating from about 5 minutes to about 30 minutes, preferably up to 60 minutes, at a temperature of under 37° C. or 4° C., a first complex is formed which includes the cellular target bound to the first labeled ligand. Various optional washing steps can be employed after the addition of the components, depending upon required assay sensitivity. The final step of this method is a simultaneous analysis of the sample treated as described above, by taking the hES-derived cell population samples containing these complexes and discriminating between the complex comprising the cellular target bound to the first labeled ligand and/or antibody and any of the sample that did not bind to the soluble ligand. The amount of first complex detected is proportional to the amount of the particular cell type having the single cellular target present in the hES-derived cell population.

As with the above assay, some embodiments described herein provide for measurement of more than one cell type, more than one cellular target on a cell type, or more than one soluble analyte by selecting from among any number of soluble ligands, detectable labels, and solid phase capture media on which is immobilized different ligands or competing analytes. Methods suitable for performing the analysis step include image analysis and, preferably, flow cytometric analysis. A flow cytometric analysis is conducted by employing a gating strategy appropriate to the sample type. For example, the complexes containing the beads are gated separately from the complex of the ligand-labeled cells based on light scatter and fluorescence intensity. Thereafter, if more than one fluorescent label is present on the cell target or the bead, the strategy can provide separate compensation for each fluorophore. Similarly other cell parameters, such as differential and intracellular antigens or other targets can also be measured during this analysis.

Some embodiments also include a number of optional steps. For example, where increased sensitivity of the assays are desirable, washing steps with buffer, or diluent can be introduced into the methods. Generally, such washing steps can be introduced after the incubation of the sample with the capture medium to eliminate materials not bound to the capture medium. Alternatively, such washing steps can follow incubation with soluble ligand to eliminate uncomplexed materials.

Additionally, embodiments described herein encompass various media to be used and including commercially available media such as Dulbecco's Modified Eagle Medium (dMEM), Hank's Basic Salt Solution (HBSS), Dulbecco's phosphate buffered saline (dPBS), RPMI, Iscove's modified Dulbecco's medium (IMDM), phosphate buffered saline (PBS) with 5 mM EDTA, etc., frequently supplemented with fetal calf serum (FCS), bovine serum albumin (BSA), human serum albumin (HSA), StemPro®hESC SFM (Novocell defined media licensed to and sold by Invitrogen) etc.

Using the methods described herein, cell populations or cell cultures can be enriched in cell content by at least about 2- to about 1000-fold as compared to untreated cell populations or cell cultures. In some embodiments, hES-derived cells can be enriched by at least about 5- to about 500-fold as compared to untreated cell populations or cell cultures. In other embodiments, hES-derived cells can be enriched from at least about 10- to about 200-fold as compared to untreated cell populations or cell cultures. In still other embodiments, hES-derived cells can be enriched from at least about 20- to about 100-fold as compared to untreated cell populations or cell cultures. In yet other embodiments, endocrine precursor cells can be enriched from at least about 40- to about 80-fold as compared to untreated cell populations or cell cultures. In certain embodiments, hES-derived cells can be enriched from at least about 2- to about 20-fold as compared to untreated cell populations or cell cultures.

Kits

For convenience, in some embodiments the conventional reagents for high throughput assays or other diagnostic assays can be provided in the form of kits. In some embodiments, a kit is provided for performance of the above-described methods. In preferred embodiments, such kits are employed for performing the diagnostic methods described herein and/or monitoring therapy. In other embodiments, such kits are assembled for research purposes also. Thus, in preferred embodiments a kit contains the components taught above, e.g., at least one soluble ligand that binds a cellular target in the sample; at least one soluble ligand that binds a soluble analyte in the sample or at least one competing soluble analyte (preferably labeled); and a solid phase capture medium that binds directly to the soluble analyte, indirectly to the soluble analyte, or to the soluble ligand that binds to the soluble analyte. The kits also include instructions for performing the particular assay, various diluents and buffers, and signal-generating reagents, such as fluorophores, enzyme substrates, cofactors and chromogens. Other components can include indicator charts for colorimetric comparisons, disposable gloves, decontamination instructions, applicator sticks or containers, and a sample preparator cup.

In one embodiment, a kit useful for the performance of the above-described immuno assays include, as a component, a solid matrix or a solid phase capture medium associated with multiple first ligands that bind the cellular marker or target and is associated with a first detectable label. The kit further comprises a second, third and/or fourth ligand that is capable of binding to a second, third and/or fourth cellular marker or target and or soluble analyze. The second, third and/or fourth ligands are associated with a second, third and/or fourth detectable label.

In another embodiment, a kit for performing another of the competitive inhibition assays described above, contains a first ligand associated with a first label. Multiple of the first ligands are capable of binding to a single cellular target. Another component is a competing analyte associated with a second label. Still another component is the solid phase capture medium on which are immobilized multiple of ligands or antibodies capable of binding to the soluble analyte (either competing soluble analyte or soluble analyte naturally occurring in the sample).

In yet another embodiment, a kit for performing the immune complex assay includes a first ligand capable of binding to a first cellular target and providing a first detectable signal; a second ligand capable of binding to the soluble analyte and providing a second detectable signal; a third ligand capable of binding to the same soluble analyte; a solid phase capture medium on which is immobilized multiple fourth ligands, the fourth ligands capable of binding to the third ligands.

Such kits are useful for evaluating hES populations and/or hES-derived cell population samples for purposes of enriching, isolating, depleting, separating, sorting, purifying and/or determining levels of certain cell types or bound components or soluble antigens or analytes thereof. Such a diagnostic kit contains the dyes, ligands, capture medium, and other components of the embodiments described herein. Such kits also contain labels, exemplified above, pre-attached to the other components of the specific assay to be performed, or provided separately for attachment to a selected component, e.g., a substrate. Alternatively, such kits can contain a simple mixture of such compositions or means for preparing a simple mixture.

Having generally described certain embodiments, a further understanding can be obtained by reference to certain specific examples which are provided herein for purposes of illustration only, and are not intended to be limiting.

EXAMPLE 1

Human ES-Derived cell Specific CD antigens

To enable isolation and purification of hES-derived cells, such as human definitive endoderm cells, gut endoderm cells, pancreatic epithelial cells and/or pancreatic endoderm type cells, or endocrine cells from human embryonic stem cells (hESCs), a high-throughput flow cytometry based screen of antibodies was performed to determine novel cell surface antigens on the hES-derived cells. The antibodies were obtained from 3 different companies including BD Pharmingen™ (La Jolla, Calif.), Biolegend (San Diego, Calif.), and Millipore Corporation (Temecula, Calif.). The antibodies obtained from BD Pharmingen were a generous gift. The antibodies are set forth in Table 1 below.

TABLE 1

| | | | ANTIBODIES | | | | |
|---|---|---|---|---|---|---|---|
| Isotype | Antigen | Antibody Clone | Company | Catalog # | CyT203 stage 2 | CyT203 stage 5 | CyT49 stage 4 |
| Ms IgG1, k | CD1d | CD1d42 | BD | 550254 | rare | − | − |
| Ms IgG1, k | CD6 | M-T605 | BD | 555356 | rare | − | − |
| Ms IgG1, k | CD9 | M-L13 | BD | 555370 | + | + | + |
| Ms IgG1, k | CD10 | HI10a | BD | 555373 | + | + | + |
| Ms IgG1, k | CD13 | WM15 | BD | 555393 | + | + | + |
| Ms IgM, k | CD15 | HI98 | BD | 555400 | + | + | + |
| Ms IgG2a, k | CD24 | ML5 | BD | 555426 | + | + | + |
| Ms IgG1, k | CD25 | M-A251 | BD | 555430 | rare | rare | − |
| Ms IgG1, k | CD26 | M-A261 | BD | 555435 | + | + | + |
| Ms IgG1, k | CD27 | M-T271 | BD | 555439 | − | rare | − |
| Ms IgG2a, k | CD29 | HUTS-21 | BD | 556048 | + | + | + |
| Ms IgG1, k | CD30 | BerH8 | BD | 555827 | + | − | − |
| Ms IgG1, k | CD31 | WM59 | BD | 555444 | + | − | − |
| Ms IgG2b, k | CD32 | FLI8.26 | BD | 555447 | − | − | rare |
| Ms IgG1, k | CD34 | 581 | BD | 555820 | + | + | + |
| Ms IgM, k | CD36 | CB38 (NL07) | BD | 555453 | rare | − | − |
| Ms IgG1, k | CD40 | 5C3 | BD | 555587 | + | − | − |
| Ms IgG2b, k | CD44 | G44-26 | BD | 555476 | + | − | − |
| Ms IgG2a, k | CD45RO | UCHL1 | BD | 555491 | rare | − | − |
| Ms IgG2a, k | CD46 | E4.3 | BD | 555948 | + | + | + |
| Ms IgG1, k | CD47 | B6H12 | BD | 556044 | + | + | + |
| Ms IgM, k | CD48 | T00dc145 | BD | 555758 | rare | − | − |
| Ms IgG1, k | CD49a | SR84 | BD | 559594 | + | + | + |
| Ms IgG1, k | CD49b | AK-7 | BD | 555497 | + | + | + |
| Ms IgG2a, k | CD49b | 12F1-H6 | BD | 555668 | + | + | + |
| Ms IgG1, k | CD49c | C3 II.1 | BD | 556024 | + | + | + |
| Ms IgG1, k | CD49e | IIA1 | BD | 555615 | + | + | + |
| Ms IgG1, k | CD49e | VC5 | BD | 555651 | + | + | + |
| Ms IgG2a, k | CD49f | GoH3 | BD | 555734 | rare | − | − |
| Ms IgG2b, k | CD50 | T00dc41 | BD | 555957 | + | − | − |
| Ms IgG1, k | CD54 | HA58 | BD | 555510 | + | − | + |
| Ms IgG2a, k | CD55 | IA10 | BD | 555691 | + | + | + |

TABLE 1-continued

ANTIBODIES

| Isotype | Antigen | Antibody Clone | Company | Catalog # | CyT203 stage 2 | CyT203 stage 5 | CyT49 stage 4 |
|---|---|---|---|---|---|---|---|
| Ms IgG2b, k | CD56 | NCAM16.2 | BD | 559043 | + | + | + |
| Ms IgM, k | CD57 | NK-1 | BD | 555618 | + | + | + |
| Ms IgG2a, k | CD58 | 1C3 | BD | 555919 | + | + | + |
| Ms IgG2a, k | CD59 | p282 (H19) | BD | 555761 | + | + | + |
| Ms IgG1, k | CD61 | VI-PL2 | BD | 555752 | rare | − | rare |
| Ms IgG1, k | CD62E | 68-5H11 | BD | 555648 | − | − | rare |
| Ms IgG1, k | CD63 | H5C6 | BD | 556019 | + | + | + |
| Ms IgG1, k | CD66 | B6.2/CD66 | BD | 551355 | + | + | + |
| Ms IgM, k | CD66b | G10F5 | BD | 555723 | rare | − | − |
| Ms IgG2a, k | CD71 | M-A712 | BD | 555534 | + | + | + |
| Ms IgG1, k | CD73 | AD2 | BD | 550256 | − | + | + |
| Ms IgM, k | CD77 | 5B5 | BD | 551352 | rare | − | − |
| Ms IgG1, k | CD79b | CB3.1 | BD | 555678 | rare | rare | − |
| Ms IgG1, k | CD81 | JS-81 | BD | 555675 | + | + | + |
| Ms IgG1, k | CD83 | HB15e | BD | 556854 | rare | rare | rare |
| Ms IgG2b, k | CD85 | GHI/75 | BD | 555941 | rare | − | − |
| Ms IgG1, k | CD90 | 5E10 | BD | 555593 | + | + | + |
| Ms IgG1, k | CD91 | A2MR-alpha 2 | BD | 550495 | + | + | + |
| Ms IgG2b | CD93 | R139 | Millipore | MAB4314 | rare | rare | nd |
| Ms IgG1, k | CD95 | DX2 | BD | 555671 | − | + | + |
| Ms IgG1, k | CD98 | UM7F8 | BD | 556074 | + | + | + |
| Ms IgG2a, k | CD99 | T00dc12 | BD | 555687 | + | + | + |
| Ms IgM, k | CD99R | HIT4 | BD | 555817 | + | − | + |
| Ms IgG1, l | CD104 | 450-9D | BD | 555721 | + | − | − |
| Ms IgG1, k | CD105 | 43A3 | Biolegend | 323201 | rare | rare | nd |
| Ms IgG1, k | CD106 | 51-10C9 | BD | 555645 | + | − | − |
| Ms IgG2a, k | CD108 | KS-2 | BD | 552423 | + | − | − |
| Ms IgG1, k | CD112 (PRR2) | R2.525 | BD | 551056 | − | + | − |
| Ms IgG1, K | CD116 | 4H1 | Biolegend | 305901 | + | − | − |
| Ms IgG1, k | CD117 | YB5.B8 | BD | 555713 | + | − | − |
| Ms IgG1, k | CD123 | 9F5 | BD | 555642 | − | − | rare |
| Ms IgG1, k | CD130 | AM64 | BD | 555756 | + | + | + |
| Ms IgG1, k | CD134 | ACT35 | BD | 555836 | rare | − | − |
| Ms IgG1, k | CD138 | Mi15 | BD | 551902 | rare | − | − |
| Ms IgG2a, k | CD140a | alpha R1 | BD | 556001 | + | + | − |
| Ms IgG2a, k | CD140b | 28D4 | BD | 558820 | + | + | + |
| Ms IgG1, k | CD141 | 1A4 | BD | 559780 | + | + | + |
| Ms IgG1, k | CD142 | HTF-1 | BD | 550252 | + | + | + |
| Ms IgG1, k | CD146 | P1H12 | BD | 550314 | + | + | + |
| Ms IgG1, k | CD147 | HIM6 | BD | 555961 | + | + | + |
| Ms IgG1, k | CD150 | A12 | BD | 559591 | − | rare | − |
| Ms IgG1, k | CD151 | 14A2.H1 | BD | 556056 | + | + | + |
| Ms IgG1, k | CD153 | D2-1173 | BD | 550052 | rare | − | − |
| Ms IgM, k | CD158a | HP-3E4 | BD | 556061 | rare | − | − |
| Ms IgG2a, k | CD164 | N6B6 | BD | 551296 | + | + | + |
| Ms IgG1, k | CD165 | SN2 | BD | 556050 | + | + | + |
| Ms IgG1, k | CD166 | 3A6 | BD | 559260 | + | + | + |
| Ms IgG1, K | CD172a | SE5A5 | Biolegend | 323801 | + | + | + |
| Ms IgG1, k | CD172b | B4B6 | BD | 552024 | − | rare | − |
| Ms IgG1, k | CD177 | MEM-166 | BD | 551899 | + | + | + |
| Ms IgG2a, k | CD184 | 12G5 | BD | 555972 | + | + | + |
| Ms IgG1, k | CD200 | MRC OX-104 | BD | 552023 | + | + | + |
| Rat IgG1, k | CD201 | RCR-252 | BD | 552500 | − | rare | − |
| Ms IgG2b, k | CD209 | DCN46 | BD | 551186 | rare | rare | − |
| Ms IgG1, K | CD218a | H44 | Biolegend | 313803 | rare | − | − |
| Ms IgG1, k | CD220 | 3B6/IR | BD | 559954 | + | + | + |
| Ms IgG1, k | CD221 | 3B7 | BD | 556000 | + | + | + |
| Ms IgG1, K | CD222 | MEM-238 | Biolegend | 315901 | + | + | + |
| Ms IgG1, k | CD227 | HMPV | BD | 555925 | + | + | + |
| Ms IgG1, K | CD261 | DJR1 | Biolegend | 307201 | − | rare | rare |
| Ms IgG1, K | CD266 | ITEM-1 | Biolegend | 314001 | + | + | + |
| Ms IgG2b, K | CD318 | CUB1 | Biolegend | 324001 | + | + | + |
| Ms IgG1, K | CD334 | 4FR6D3 | Biolegend | 324305 | + | n.d. | n.d. |
| Ms IgG1, K | CD340 | 24D2 | Biolegend | 324401 | + | + | + |
| Ms IgG2b, k | ABCG2 | 5D3 | BD | 552823 | + | + | − |
| Ms IgM, k | αβ TCR | T10B9.1A-31 | BD | 555546 | rare | − | − |
| Ms IgM, k | β2-microglobulin | T00dc99 | BD | 555550 | + | − | − |
| Ms IgG3, k | Blood Group A | NaM87-1F6 | BD | 550806 | + | + | + |
| Ms IgM, k | CMRF44 | CMRF44 | BD | 551055 | − | + | − |
| Rat IgM, k | CLA | HECA-452 | BD | 555946 | − | rare | − |
| Ms IgG2b, k | EGF Receptor | EGFR1 | BD | 555996 | + | + | + |

TABLE 1-continued

ANTIBODIES

| Isotype | Antigen | Antibody Clone | Company | Catalog # | CyT203 stage 2 | CyT203 stage 5 | CyT49 stage 4 |
|---|---|---|---|---|---|---|---|
| Ms IgG1, k | F11 Receptor | M.AB.F11 | BD | 552147 | + | + | + |
| Ms IgG1, k | fMLP receptor | 5F1 | BD | 556015 | − | rare | − |
| Ms IgG1, k | γδTCR | B1 | BD | 555715 | − | rare | − |
| Ms IgG1, k | HLA-A, B, C | G46-2.6 | BD | 555551 | + | + | + |
| Ms IgG2b, k | HLA-A2 | BB7.2 | BD | 551230 | + | − | − |
| Ms IgG1, k | mu-Calpain | B27D8 | BD | 550935 | − | − | + |
| Ms IgG1, k | NGF receptor | C40-1457 | BD | 557194 | + | − | + |
| Ms IgG1, k | Siglec-6 | E20-1232 | BD | 550908 | + | − | + | hESC culture preparation: Human embryonic stem cells (hESCs; CyT49 and CyT203 lines) were differentiated in vitro to either stage 2 for about 5-6 days or to stage 4 or 5 for about 13-22 days substantially as described in D'Amour et al. 2006 Nat. Biotechnol. 24(11): 1392-401 and U.S. patent application Publication Number 2007/0154984, the disclosures of which are incorporated herein by reference in their entireties. Briefly, undifferentiated human embryonic stem (hES) cells were maintained on mouse embryo fibroblast feeder layers (Millipore, formerly Chemicon or Specialty Media) or on human serum coated plates (Valley Biomedical) in DMEM/F12 (Mediatech) supplemented with 20% Knock-Out serum replacement (Invitrogen/Gibco), 1 mM nonessential amino acids (Invitrogen/Gibco), Glutamax (Invitrogen/Gibco), penicillin/streptomycin (Invitrogen/Gibco), 0.55 mM 2-mercaptoethanol (Invitrogen/Gibco) and 4 ng/ml to 20 ng/mL recombinant human FGF2 (R&D Systems). Activin A (R&D Systems) was added to the growth culture medium at 10-25 ng/ml to help maintain undifferentiated growth. Cultures were either manually passaged, passaged using 5 ug/mL dispase (Invitrogen/Gibco), or passaged using Accutase (Innovative Cell Technologies #AT104) at 1:4-1: 15 split ratios every 3-7 days. Before initiating differentiation, hES cells were given a brief wash in PBS+/+ (Mediatech).

Differentiation: Human ES cells were differentiated in RPMI (Mediatech) supplemented with Glutamax, penicillin/streptomycin, 100 ng/mL activin A and varying concentrations of defined FBS (HyClone). Additionally, 0.1% BSA (Invitrogen/Gibco) and 25 ng/mL-75 ng/ml Wnt3a was added on the first day (d0) of differentiation. In most differentiation experiments FBS concentrations were 0% for the first 24 h, 0.2% for the second 24 h, and 0.2% for the third 24h, when a third stage 1 day was used. Recombinant human activin A and Wnt3a were purchased from R&D Systems.

Subsequently, at stage 2, cells were briefly washed in PBS+/+ and then differentiated in RPMI supplemented with 2% FBS, Glutamax, penicillin/streptomycin, and 25 ng-50 ng/mL KGF (R&D Systems) for 3 days. In some experiments 5 uM SB431542 (Sigma Aldrich, Inc.) was added during the first day of stage 2.

Subsequently (stage 3), cells were differentiated in DMEM (Hyclone) supplemented with Glutamax, penicillin/stretopmycin, and 0.5×B27-supplement (Invitrogen/Gibco). Media was additionally supplemented with either 1 uM to 2 uM Retinoic acid (Sigma) and 0.25 nM kaad-cyclopamine (Toronto Research Chemicals) for 1 to 3 days. In other cases noggin was added at 50 ng/mL (R&D systems) along with the retinoic acid and kaad-cyclopamine. Alternatively, 0.2 uM to 0.5 uM retinoic acid and 0.25 nm Kaad-cyclopamine was added to the media for one day. In some experiments no retinoic acid or kaad-cyclopmaine was added.

At stage 4, after withdrawal of retinoic acid or in cases where no retinoic acid was added, noggin at 30-100 ng/mL was added to the media for 1-9 days, and in some experiments FGF10 at 25 ng/nL was also added.

For stage 5 differentiation was continued in either CMRL (Invitrogen/Gibco) or DMEM (Hyclone) supplemented with Glutamax, penicillin/stretopmycin, and 0.5×B27-supplement (Invitrogen). In some experiments media was also supplemented with 0.5% human serum (Valley Biomedical) during stage 5.

Cells were collected at stages 2 (endodermal lineage screen), late stage 4/early stage 5 (pancreatic endoderm and endocrine screen) and stage 5 (pancreatic endoderm and endocrine screen). Cells were briefly washed in PBS. Using either TrypLE (Invitrogen #12563-011) or Accutase (Innovative Cell Technologies #AT104) at 37° C. cells were enzymatically dissociated to single cell suspension. 3 to 10% FBS/PBS was added and the suspension was passed through a 40-100 um filter and pelleted. The cells were washed in 3% FBS/PBS (buffer). Cells were pelleted and resuspended as a single cell suspension in buffer to block nonspecific antibody binding. Cells were incubated with the antibodies as described in Table 1 in a volume of 100 ul buffer containing 0.3-1×10e6 cells in a 96 well plate with 2 ul of antibody for 30-60 minutes at 4 degrees Celsius. Cells were pelleted and then washed 2 times in 2× volume buffer. Cells were then incubated in a volume of 100 ul buffer containing 0.3-1×10e6 cells in a 96 well plate with 2.5 ul of the appropriate fluorochrome conjugated secondary antibody for 30-60 minutes at 4 degrees Celsius. Cells were pelleted and then washed 2 times in 2× volume buffer. 0.3-1×10e6 cells were then resuspended in 200 ul-350 ul volume of 1% paraformaldehyde (Alfa Aesar) and placed in microdilution tubes for flow cytometry analysis.

Flow cytometry analysis was performed on a FACSCalibur™ (Becton Dickinson), according to the manufacturer's instructions and analyzed using FlowJo flow cytometry analysis software (Tree Star, Inc.). Each sample containing a cell sample and contacting each of the above antibodies in Table 1 was analyzed. Cells were gated for intact cells using the parameters of forward and side scatter, and subsequently intact cells were analyzed for fluorescence intensity. In some cases, additional gating of intact cells was performed to separate cells into sub-populations on the parameters of forward and side scatter. Those antibodies with fluorescent intensity levels at least 3× above the standard control were characterized as positive, represented by a "+" sign in Table 1. Those antibodies with fluorescent intensity levels at least 3× below the standard control were characterized as negative, represented by a "−" sign in Table 1. Finally, those antibodies which stained <=0.5-1% of the intact cells were characterized as rare as stated in Table 1. Some samples having fluorescent intensity levels at least 3× above the standard controls were characterized further, and at least those samples with anti-CD30, CD49a, CD49e, CD55, CD57, CD98, CD99, CD142, CD165, CD200, CD318, CD334, and CD340, are described in detail below in Examples 2 through 6.

Based on the data presented in Table 1, any of the antibodies that resulted in positive or rare staining could be used for positive or negative immuno-selection of hES-derived endoderm populations at various stages of differentiation.

EXAMPLE 2

Purification of Gut Endoderm Cells Using CD30, CD49A, CD49E, CD55, CD99, CD165, and CD334

To further characterize some of the antibodies described in Example 1/Table 1, cells were co-stained with both the anti-surface marker antibody and an antibody to a known marker of gut endoderm, the transcription factor FOXA2. Briefly, CyT203 hES cells were differentiated substantially as described in Example 1. On day 6 differentiated cells were collected and enzymatically digested to a single cell suspension, resuspended in buffer (3% FBS/PBS), and stained with primary antibodies to cell surface markers as described in Example 1 except that in some cases staining was performed in tubes and post-antibody washes with buffer were typically performed 1-2× with a 10× volume of buffer. Cells were incubated in a 1:10 dilution of the following fluorochrome-conjugated or unconjugated antibodies, some of which are also listed in Table 1: anti-CD55-PE (BD Biosciences #555694), CD49a (BD Biosciences #559594), CD49e-PE (BD Biosciences #555617), CD334-PE (Biolegend #324305), CD30 (BD Biosciences #555827), CD99 (BD Biosciences #555687), and CD165 (BD Biosciences #556050).

Following incubation with primary and appropriate secondary antibodies, the cells were fixed in 4% paraformaldehyde for 30 minutes and then washed and stored in buffer. For intracellular or intranuclear staining, cells were permeabilized for 30 minutes on ice in PBS containing 5% normal donkey serum (Jackson Immunoresearch) and 0.2% Triton X-100 and then washed in buffer. Cells were then incubated overnight at 4 degrees Celsius in PBS containing 5% normal donkey serum and 0.1% Triton X-100 (blocking buffer) and a 1:100 dilution of anti-FOXA2 antibody (Santa Cruz #6554). Cells were then washed in buffer and subsequently incubated in blocking buffer containing the appropriate secondary antibody for 60 minutes at 4 degrees Celsius. Cells were washed 2× in buffer and then resuspended in buffer or 1% paraformaldehyde for flow cytometry analysis. Flow cytometry analysis was performed as described in Example 1.

Flow cytometry analyses of either anti-CD30, CD49a or CD55 co-staining with anti-FOXA2 are shown in Table 2. 38.70% CD30-FOXA2+ cells and a total of 44.87% FOXA2+ cells were present in the cell population. CD30+ cells comprised 86.25% of the total FOXA2+ cells, making CD30 a useful marker for negative selection of gut endoderm. 28.91% CD49a(low)FOXA2+ cells and a total of 39.29% FOXA2+ cells were present in the population. CD49a(low) cells comprised 73.58% of the total FOXA2+ cells, making CD49a a useful marker for negative selection of gut endoderm. 26.50% CD55(low)FOXA2+ cells and a total of 37.50% FOXA2+ cells were present in the population. CD55− cells comprised 70.67% of the total FOXA2+ cells, making CD55 useful for negative selection of gut endoderm.

TABLE 2

CD30, CD49A OR CD55 NEGATIVE IMMUNO-SELECTION FOR FOXA2+ GUT ENDODERM

|  | CD30−<br>FOXA2+ | CD30+<br>FOXA2+ | CD30+<br>FOXA2− | CD30−<br>FOXA2− | Total<br>FOXA2+ | Total<br>FOXA2− | % of total FOXA2+<br>cells that are CD30− |
|---|---|---|---|---|---|---|---|
| CD30 | 38.70% | 6.17% | 28.80% | 26.30% | 44.87% | 55.10% | 86.25% |

|  | CD49a(low)<br>FOXA2+ | CD49a(high)<br>FOXA2+ | CD49a(high)<br>FOXA2− | CD49a(low)<br>FOXA2− | Total<br>FOXA2+ | Total<br>FOXA2− | % of total FOXA2+<br>cells that are<br>CD49a(low) |
|---|---|---|---|---|---|---|---|
| CD49a | 28.91% | 10.38% | 44.21% | 16.38% | 39.29% | 60.59% | 73.58% |

|  | CD55(low)<br>FOXA2+ | CD55(high)<br>FOXA2+ | CD55(high)<br>FOXA2− | CD55(low)<br>FOXA2− | Total<br>FOXA2+ | Total<br>FOXA2− | % of total FOXA2+<br>cells that are<br>CD55(low) |
|---|---|---|---|---|---|---|---|
| CD55 | 26.50% | 11.00% | 43.50% | 19.10% | 37.50% | 62.60% | 70.67% |

Flow cytometry analyses of either anti-CD49e, CD99, CD165, or CD334 co-staining with anti-FOXA2 are shown in Table 3. About 30.00% CD49e(high)FOXA2+ cells and a total of 39.47% FOXA2+ cells were present in the cell population. CD49e(high) cells comprised 76.01% of the total FOXA2+ cells, and hence CD49e can be utilized for positive immuno-selection of gut endoderm. Similarly, CD99(high) cells comprised 92.72% and CD165+ cells comprised 99.12% of the total FOXA2+ cells. CD99 or CD165 can therefore be utilized for positive immuno-selection of gut endoderm as well. CD334+ cells comprised 28.88% of the total FOXA2+ cells and 3.6% of the total FOXA2− cells. Hence, CD334 can also be used for positive immuno-selection of gut endoderm.

gated antibodies: CD55-PE (BD Biosciences #555694), CD55-APC (BD Biosciences #555696), CD57-FITC (BD Biosciences #555619), CD98-FITC (BD Biosciences #556076), CD98-PE (BD Biosciences #556077), CD142-PE (BD Biosciences #550312). Cells were then processed for intracellular or intranuclear staining substantially as described in Example 2 except that post primary antibody and post secondary antibody washes and incubation in secondary antibody was performed in PBS containing 1% bovine serum albumin. A 1:5000 dilution of PDX1 antibody (gift from Chris Wright, Vanderbilt University) was used. Flow cytometric analysis was performed substantially as described in Example 1. The results of the flow analyses are presented in Tables 4, 5, and 6

TABLE 3

CD49e, CD99, CD165, or CD334 positive immuno-selection for FOXA2+ gut endoderm

| | CD49e(low) FOXA2+ | CD49e(high) FOXA2+ | CD49e(high) FOXA2− | CD49e(low) FOXA2− | Total FOXA2+ | Total FOXA2− | % of total FOXA2+ cells that are CD49e(high) |
|---|---|---|---|---|---|---|---|
| CD49e | 9.47% | 30.00% | 19.10% | 41.50% | 39.47% | 60.60% | 76.01% |

| | CD165− FOXA2+ | CD165+ FOXA2+ | CD165+ FOXA2− | CD165− FOXA2− | Total FOXA2+ | Total FOXA2− | % of total FOXA2+ cells that are CD165+ |
|---|---|---|---|---|---|---|---|
| CD165 | 0.37% | 41.70% | 40.60% | 17.30% | 42.07% | 57.90% | 99.12% |

| | CD334− FOXA2+ | CD334+ FOXA2+ | CD334+ FOXA2− | CD334− FOXA2− | Total FOXA2+ | Total FOXA2− | % of total FOXA2+ cells that are CD334+ |
|---|---|---|---|---|---|---|---|
| CD334 | 29.80% | 12.10% | 2.10% | 56.00% | 41.90% | 58.10% | 28.88% |

| | CD99− FOXA2− | CD99− FOXA2+ | CD99(low) FOXA2+ | CD99(high) FOXA2+ | CD99(high) FOXA2− | CD99(low) FOXA2− | Total FOXA2+ | Total FOXA2− | % of total FOXA2+ cells that are CD99(high) |
|---|---|---|---|---|---|---|---|---|---|
| CD99 | 14.16% | 0.74% | 2.26% | 38.20% | 16.93% | 27.70% | 41.20% | 58.79% | 92.72% |

EXAMPLE 3

Purification of PDX1 Endoderm Cells Using CD55, CD57, CD98, and CD142

To further characterize some of the antibodies described in Example 1/Table 1, cells were co-stained with both the anti-surface marker antibody (Table 1) and an antibody to the transcription factor PDX1, a marker of posterior foregut endoderm and pancreatic endoderm. CyT49 hES cells were differentiated substantially as described in Example 1. Differentiated cells were then collected on day 14 and processed for surface antibody staining as described in Examples 1 and 2 using a 1:10 dilution of the following fluorochrome conju- Flow cytometric analyses of either anti-CD55 or CD98 co-stained with anti-PDX1 are shown in Table 4. 15.60% CD55-PDX1+ cells and a total of 25.90% PDX1+ cells were present in the population. CD55− cells comprised 60.23% of the total PDX1+ cells, making CD55 useful for negative immuno-selection of PDX1+ endoderm. Similarly, CD98− cells comprised 39.94% of the total PDX1+ cells in the population making CD98 useful for negative immuno-selection of PDX1+ endoderm.

TABLE 4

CD55 OR CD98 NEGATIVE IMMUNO-SELECTION FOR PDX1 ENDODERM

| | CD55− PDX1+ | CD55+ PDX1+ | CD55+ PDX1− | CD55− PDX1− | Total PDX1+ | Total PDX1− | % of total PDX1+ cells that are CD55− |
|---|---|---|---|---|---|---|---|
| CD55 | 15.60% | 10.30% | 47.70% | 26.40% | 25.90% | 74.10% | 60.23% |

| | CD98− PDX1+ | CD98+ PDX1+ | CD98+ PDX1− | CD98− PDX1− | Total PDX1+ | Total PDX1− | % of total PDX1+ cells that are CD98− |
|---|---|---|---|---|---|---|---|
| CD98 | 8.58% | 12.90% | 72.00% | 6.52% | 21.48% | 78.52% | 39.94% |

Results of flow cytometric analyses of either anti-CD57 or CD142 co-stained with anti-PDX1 are shown in Table 5. 21.20% CD57+PDX1+ cells and a total of 26.10% PDX1+ cells were present in the population. CD57+ cells comprised 81.23% of the total PDX1+ cells, making CD57 useful for positive immuno-selection of PDX1+endoderm. Similarly, CD 142+ cells comprised 79.30% of the total PDX1+ cells in the population making CD 142 useful for positive immuno-selection of PDX1+ endoderm.

TABLE 5

CD57 OR CD142 POSITIVE IMMUNO-SELECTION FOR PDX1 ENDODERM

|  | CD57−<br>PDX1+ | CD57+<br>PDX1+ | CD57+<br>PDX1− | CD57−<br>PDX1− | Total<br>PDX1+ | Total<br>PDX1− | % of total PDX1+<br>cells that are<br>CD57+ |
|---|---|---|---|---|---|---|---|
| CD57 | 4.90% | 21.20% | 29.10% | 44.80% | 26.10% | 73.90% | 81.23% |

|  | CD142−<br>PDX1+ | CD142+<br>PDX1+ | CD142+<br>PDX1− | CD142−<br>PDX1− | Total<br>PDX1+ | Total<br>PDX1− | % of total PDX1+<br>cells that are<br>CD142+ |
|---|---|---|---|---|---|---|---|
| CD142 | 4.32% | 16.40% | 23.60% | 55.70% | 20.72% | 79.30% | 79.15% |

Results of flow cytometric analyses of either anti-CD55, CD142 and PDX1 or CD98, CD142, and anti-PDX1 co-staining are shown in Table 6. The CD55-CD142+ population was comprised of 83.40% PDX1+ cells and the CD98-CD142+ population was comprised of 90.20% PDX1+ cells. Therefore, either CD55 or CD98 with CD142 can be used to immuno-select for a >80% PDX1+endoderm cell population.

TABLE 6

COMBINING CD55 OR CD98 NEGATIVE WITH CD142 FOR POSITIVE IMMUNO-SELECTION FOR PDX1 ENDODERM

|  | CD55−<br>CD142+ | CD55+<br>CD142+ | CD55+<br>CD142− | CD55−<br>CD142− | CD55−<br>CD142+<br>PDX1+ | CD55+<br>CD142+<br>PDX1+ | CD55+<br>CD142−<br>PDX1+ | CD55−<br>CD142−<br>PDX1+ | Total<br>PDX1+ | % of total CD55−<br>CD142+ cells that<br>are PDX1+ |
|---|---|---|---|---|---|---|---|---|---|---|
| CD55<br>CD142 | 10.40% | 22.20% | 48.90% | 18.50% | 8.67% | 10.57% | 2.97% | 3.20% | 25.41% | 83.40% |

|  | CD98−<br>CD142+ | CD98+<br>CD142+ | CD98+<br>CD142− | CD98−<br>CD142− | CD98−<br>CD142+<br>PDX1+ | CD98+<br>CD142+<br>PDX1+ | CD98+<br>CD142−<br>PDX1+ | CD98−<br>CD142−<br>PDX1+ | Total<br>PDX1+ | % of total CD98−<br>CD142+ cells that<br>are PDX1+ |
|---|---|---|---|---|---|---|---|---|---|---|
| CD98<br>CD142 | 8.17% | 20.30% | 57.90% | 13.60% | 7.37% | 7.55% | 2.53% | 3.67% | 21.12% | 90.20% |

To examine which cell types were marked by the anti-CD142 antibody, HESC differentiated stage 5 cultures were analyzed by employing immunofluorescence cytochemistry using the mouse anti-CD142 antibody (BD Pharmingen #550252), a goat anti-PDX1 antibody (gift from Chris Wright), and a rabbit anti-chromogranin A antibody (Dako-Cytomation). Cell cultures and culture conditions were substantially similar to those described above in Example 1 and in D'Amour et al. 2005 and 2006 supra. Briefly, cells were washed with PBS and then fixed in 4% paraformaldehyde for 15 minutes at 24 degrees Celsius. Plates were washed at least 2 times with PBS. Cells were incubated in 5% normal donkey serum (Jackson Immunoresearch Laboratories, Inc.)/PBS/0.1% Triton X-100 (Sigma) for 15-60 minutes. Cells were then incubated overnight at 4 degrees Celsius in 5% normal donkey serum/PBS/0.1% Triton X-100 containing the mouse anti-CD142 antibody (BD Pharmingen #550252 at 1:20), a goat anti-PDX1 antibody (gift from Chris Wright at 1:2000), and a rabbit anti-chromogranin A antibody (DakoCytomation at 1:200). Cells were washed at least 3 times in PBS/0.1% Triton X-100, and then incubated for 1-4 hours at 24 degrees Celsius in 5% normal donkey serum/PB S/0.1% Triton X-100 containing a 1:500 dilution of the following fluorochrome conjugated secondary antibodies: donkey anti-mouse AlexaFluor 555 (Invitrogen/Molecular Probes), donkey anti-goat AlexaFluor 488 (Invitrogen/Molecular Probes), and donkey anti-rabbit Cy5 (Jackson Immunoresearch Laboratories, Inc.). Cells were washed at least 2 times in PB S/0.1% Triton X-100, and then washed at least 2× in PBS. Cell nuclei were identified by incubating the cells for about 10 minutes in PBS containing 1ug/mL DAPI. Cells were washed 2× in PBS and then analyzed using confocal microscopy (Nikon Eclipse 80i, Ci).

Immunofluorescent cytochemistry confirmed the presence of CD142 membrane staining on many PDX1-immunoreactive endoderm cells (green). However CD142 staining was not substantially observed on Chromogranin A-immunoreactive endocrine cells.

EXAMPLE 4

Purification of Endocrine Cells Using CD57, CD142, CD200, CD318, and CD340

To further characterize some of the antibodies described in Example 1/Table 1, cells were co-stained with the anti-surface marker antibody (Table 1), an antibody to a known marker of endocrine cells, chromogranin A (CHGA), and/or an antibody to the pancreatic hormone marker, insulin. CyT49 hES cells were differentiated substantially as described in Example 1. Differentiated cells were then collected on days 14 to 22 and stained with anti-surface marker antibody substantially as described in Examples 1 to 3. The following fluorochrome conjugated and unconjugated antibodies were used: CD57-FITC (BD Biosciences #555619), CD142 (BD Biosciences #550252), CD142-PE (BD Biosciences #550312), CD200 (BD Biosciences #552023), CD200-PE (BD Biosciences #552475), CD318 (Biolegend #324001), CD318-PE (Biolegend #324005), CD340-PE (Biolegend #324406), and CD340-APC (Biolegend #324407). Subsequently, intracellular or intranuclear staining was performed substantially as described in Examples 2 and 3. A 1:100 dilution of anti-CHGA antibody (DAKO #A0430) and a 1:1000 dilution of anti-insulin antibody (DAKO #A0569) were used. Flow cytometric analyses were performed substantially as described in Example 1.

The results of flow cytometric analyses of anti-CD142 or CD340 co-staining with anti-CHGA are shown in Table 7. 5.38% CD142-CHGA+ cells and 6.74% CHGA+ cells were present in the population. CD142− cells comprised 79.82% of the total CHGA+ cells, making CD142 useful for negative immuno-selection of endocrine cells. Similarly, CD340− cells comprised 51.02% of the total CHGA+ cells, making CD340 useful for negative immuno-selection of endocrine cells.

TABLE 7

CD142 OR CD340 NEGATIVE IMMUNO-SELECTION FOR ENDOCRINE CELLS

|  | CD142−<br>CHGA+ | CD142+<br>CHGA+ | CD142+<br>CHGA− | CD142−<br>CHGA− | Total<br>CHGA+ | Total<br>CHGA− | % of total<br>CHGA+ cells that<br>are CD142− |
|---|---|---|---|---|---|---|---|
| CD142 | 5.38% | 1.36% | 35.20% | 58.00% | 6.74% | 93.20% | 79.82% |

|  | CD340−<br>CHGA+ | CD340+<br>CHGA+ | CD340+<br>CHGA− | CD340−<br>CHGA− | Total<br>CHGA+ | Total<br>CHGA− | % of total<br>CHGA+ cells that<br>are CD340− |
|---|---|---|---|---|---|---|---|
| CD340 | 1.75% | 1.68% | 95.70% | 0.82% | 3.43% | 96.52% | 51.02% |

Results of flow cytometric analyses of anti-CD57, CD200, or CD318 co-stained with anti-CHGA or INS are shown in Table 8. CD57+ cells comprised 94.01% of the total number of CHGA+ cells, hence CD57 is useful for positive immuno-selection of endocrine cells. CD200+ cells comprised 98.26% of total CHGA+ cells making CD200 useful for positive immuno-selection of endocrine cells. CD318+ cells comprised 94.49% of total CHGA+ cells and 92.04% of total INS+ making CD318 a candidate for positive immuno-selection of endocrine cells.

TABLE 8

CD57, CD200 OR CD340 POSITIVE IMMUNO-SELECTION FOR ENDOCRINE CELLS

|  | CD57−<br>CHGA+ | CD57+<br>CHGA+ | CD57+<br>CHGA− | CD57−<br>CHGA− | Total<br>CHGA+ | Total<br>CHGA− | % of total<br>CHGA+ cells that<br>are CD57+ |
|---|---|---|---|---|---|---|---|
| CD57 | 0.16% | 2.51% | 34.50% | 62.90% | 2.67% | 97.40% | 94.01% |

|  | CD200−<br>CHGA+ | CD200+<br>CHGA+ | CD200+<br>CHGA− | CD200−<br>CHGA− | Total<br>CHGA+ | Total<br>CHGA− | % of total<br>CHGA+ cells that<br>are CD200+ |
|---|---|---|---|---|---|---|---|
| CD200 | 0.12% | 6.76% | 21.50% | 71.70% | 6.88% | 93.20% | 98.26% |

|  | CD318−<br>CHGA+ | CD318+<br>CHGA+ | CD318+<br>CHGA− | CD318−<br>CHGA− | Total<br>CHGA+ | Total<br>CHGA− | % of total<br>CHGA+ cells that<br>are CD318+ |
|---|---|---|---|---|---|---|---|
| CD318 | 1.75% | 30.00% | 20.60% | 47.70% | 31.75% | 68.30% | 94.49% |

|  | CD318−<br>INS+ | CD318+<br>INS+ | CD318+<br>INS− | CD318−<br>INS− | Total<br>INS+ | Total<br>INS− | % of total INS+<br>cells that are<br>CD318+ |
|---|---|---|---|---|---|---|---|
|  | 1.28% | 14.80% | 35.10% | 48.80% | 16.08% | 83.90% | 92.04% |

EXAMPLE 5

Enrichment of Pancreatic Epithelial/Endoderm Cells and Endocrine Cells Using CD142

To optimize immuno selection of hES-derived pancreatic phenotype cells, CD142 magnetic cell sorting and flow cytometry analysis was performed on various hESC differentiated cultures.

Cell cultures and culture conditions were maintained substantially as that described above in Example 1 and in D'Amour et al. 2005 and 2006 supra. hESCs (CyT49) were differentiated to stage 4 to 5 type cells. Cells were briefly washed with PBS. The cells were then enzymatically dissociated into a single cell suspension using TrypLE at 37 degrees Celsius and then 3% FBS/PBS/1 mM EDTA (sorting buffer) was added. The single cell suspension was passed through a 40-100 uM filter and then pelleted. Cells were washed in sorting buffer, pelleted and then resuspended as a single cell suspension in sorting buffer at 1×10(8) cells/mL. Cells were then incubated with Phycoerythrin conjugated anti-mouse CD142 antibody (BD PHARMIGEN™ Cat. No. 550312) at 10 ul per 1×10(7) cells for 15 minutes at 4 degrees Celsius. The cells were washed at least once with 10× volume sorting buffer. Cells were pelleted and resuspended as a single cell suspension at 1×10(8) cells/mL in sorting buffer containing a 1:5 dilution of anti-PE microbeads (Miltenyi Biotec) and incubated for 15 minutes at 4 degrees Celsius. Cells were washed at least once with a 10× volume of sorting buffer, pelleted, and resuspended as a single cell suspension at 1×10 (8) cells/ml in cold sorting buffer. Immuno-magnetic selection of CD142− positive cells was then performed substantially according to manufacturer's instructions (Miltenyi Biotec). Briefly, the single cell suspension was passed over a prewet LS MACS® cell separation column attached to the magnetic separator stand. The column was washed 3 times with 3 mls of sorting buffer. Cells that did not bind to the column were collected as the flow through fraction. The column was removed from the magnetic separator stand and the bound cells were displaced off the column using 5 mls sorting buffer and cell plunger. The cells in the bound and flow through fractions were pelleted and fixed in 4% paraformaldehyde for flow cytometry analysis. The pre-sort, bound and flow through fractions were counter-stained with anti-PDX1 and CHGA substantially as described above in Examples 3 and 4.

Flow cytometry analysis was performed substantially as described in Example 1. The results of this analysis are shown in Table 9. As shown in Table 9, the bound fraction was highly enriched for CD142+ cells compared to the pre-sorted and flow through fractions. The bound fraction was also enriched for PDX1+ cells compared to the presort and flow through fractions. The anti-CD142 bound fraction was comprised of 71.07% PDX1+ cells compared to 22.26% PDX1+ cells in the pre-sort fraction and 8.32% PDX1+ cells in the flow through fraction. Therefore, there was a 3.19 fold enrichment in PDX1+ cells in the bound fraction relative to the pre-sort population. In addition the CD142 bound fraction was depleted of CHGA+ endocrine cells compared to the pre-sort population. The pre-sort population was comprised of 11.06% CHGA+ cells whereas the bound fraction was comprised of 3.67% CHGA+ cells. Most of the CHGA+ cells were present in the flow through fraction, which was comprised of 11.22% CHGA+ cells.

TABLE 9

CD142 IMMUNO-SELECTION OF PANCREATIC EPITHELIAL AND ENDOCRINE CELLS

| | | CD142+ | CD142+ fold | PDX1+ | PDX1+ fold | CHGA+ | CHGA+ fold |
|---|---|---|---|---|---|---|---|
| Day 14 | Pre-sort | 38.33% | | 22.26% | | 11.06% | |
| | Bound | 82.59% | 2.15X | 71.07% | 3.19X | 3.67% | 0.33X |
| | Flow through | 24.66% | 0.64X | 8.32% | 0.37X | 11.22% | 1.01X |
| Day 16 | Pre-sort | 48.40% | | | | | |
| | Bound | 83.10% | 1.72X | | | | |
| | Flow through | 29.00% | 0.60X | | | | |

To determine which genes were expressed by the CD142 staining cells in the bound fraction, compared to pre-sorted cells or flow through fraction cells, total RNA was isolated from the samples with a 6100 nucleic acid extractor (Applied Biosystems) and 100-500 ng was used for reverse transcription with iScript cDNA synthesis kit (Bio-Rad). PCR reactions were run in duplicate using ¹⁄₄₀th of the cDNA per reaction and 400 nM forward and reverse primers with QuantiTect SYBR Green master mix (Qiagen). Alternatively, QuantiTect Primer Assays (Qiagen) were used according to the manufacturer's instructions. Real-time PCR was performed using the Rotor Gene 3000 (Corbett Research). Relative quantification was performed in relation to a standard curve. The standard curve was created using a mixture of total RNA samples from various fetal human endoderm tissues and differentiated hES cells, and 1 μg was used per cDNA reaction in creating the standard curve. Quantified values for each gene of interest were normalized against the input determined by two housekeeping genes (CYCG and GUSB or TBP). The standard deviation of four- or six-gene expression measurements was reported. Primer sequences: Pdx1 forward primer (5' to 3'), AAGTCTACCAAAGCTCACGCG (SEQ ID NO: 7); Pdx1 reverse primer (5' to 3'), GTAGGCGCCGCCTGC (SEQ ID NO:8).

The results of the QPCR analysis are shown in Table 10. Relative fold increases or decreases in expression of the markers between the different fractions are shown. The expression of pancreatic endoderm markers including PDX1, NKX6.1, and PTF1A were increased in the CD142 bound fraction as compared to the pre-sort and flow through fractions. The expression of endocrine markers including PAX6, INS, and GCG were decreased in the CD142 bound fraction as compared to the pre-sort and flow through fractions. The expression of pancreatic endoderm markers were decreased in the CD142 flow through fraction as compared to the pre-sort and bound fractions, whereas the expression of endocrine markers was increased in the CD142 flow through fraction as compared to the pre-sort and bound fractions. CD142 therefore can be used for positive immuno-selection to enrich pancreatic epithelial/endoderm cells, whereas the flow through fraction (the fraction or cells not binding to the antibody column; or CD142−) is enriched with pancreatic endocrine type cells.

a 1.89× increase in CHGA+ cells and a 2.43× increase in INS+ cells in the CD200 bound fraction (67.5% CHGA+ cells, 19.9% INS+ cells) as compared to the pre-sort fraction (35.7% CHGA+ cells, 8.2% INS+ cells). Further enrichment of CHGA+ and INS+ cells was observed upon aggregation of

TABLE 10

CD142 ENRICHES FOR PANCREATIC EPITHELIUM/ENDODERM AND/OR PANCREATIC ENDOCRINE TYPE CELLS

|  | PDX1 Fold Incease or Decrease | NKX6.1 Fold Increase or Decrease | PTF1A Fold Increase or Decrease | PAX6 Fold Increase or Decrease | INS Fold Increase or Decrease | GCG Fold Increase or Decrease |
|---|---|---|---|---|---|---|
| Bound/Flow Through | 15.32 | 32.87 | 21.85 | 0.18 | 0.17 | 0.11 |
| Bound/Pre-sort | 3.82 | 8.14 | 1.95 | 0.30 | 0.21 | 0.17 |
| Flow Through/Pre-sort | 0.25 | 0.25 | 0.09 | 1.69 | 1.23 | 1.56 |

These data demonstrate that CD142 is a useful marker for purifying, enriching and/or isolating for hESC-derived pancreatic epithelial type cells and endocrine cell types.

EXAMPLE 6

Enrichment of Endocrine Cells Using CD200 and CD318

Similar to that described for CD142 in example 5, characterization of CD200 and CD318 as novel cell surface markers for hESC-derived pancreatic endocrine cells from stage 5 cultures was performed by immuno-selection.

Cell cultures and culture conditions were maintained substantially as that described herein and in D'Amour et al. 2005 and 2006 supra. hESCs (CyT49) were differentiated to stage 5 type cells and immuno-selected using CD200 or CD318 antibody columns. The CD200 and CD318 bound fractions, in some cases, were cultured as cell aggregates for 2 to 4 days in either DMEM (Hyclone) or CMRL (Invitrogen) in stage 5 media as described in Example 1. The media was additionally supplemented with 50 ug/mL DNase, 2% FBS, and 10 ng/mL FGF2. Cell aggregates were dissociated to a single cell suspension using TrypLE and processed for flow cytometry analysis substantially as described in Example 5.

Flow cytometry was performed substantially as described above in Example 5. In this case, intracellular cellular staining was performed with anti-CHGA and anti-INS antibodies on the pre-sort, bound, bound aggregate, and flow through fractions as described in Examples 2-5. Results of this analysis are shown in Table 11. Immuno-selection with CD200 enriched for CHGA+ and INS+ endocrine cells as shown by a 1.89× increase in CHGA+ cells and a 2.43× increase in INS+ cells in the CD200 bound fraction (67.5% CHGA+ cells, 19.9% INS+ cells) as compared to the pre-sort fraction (35.7% CHGA+ cells, 8.2% INS+ cells). Further enrichment of CHGA+ and INS+ cells was observed upon aggregation of the CD200 bound cells. The CD200 bound aggregates were about 84% CHGA+ (2.35× enrichment) and 22.5% INS+ (2.74× enrichment). Similar enrichment in CHGA+ endocrine cells (2.91× enrichment in the CD200 bound fraction) was observed in a second CD200 immuno-selection experiment. Hence, immuno-selection with CD200 enriched for CHGA+ endocrine type cells. The CD318 bound fraction was 2.08× enriched in CHGA+ type cells (71.0% CHGA+ cells) as compared to the pre-sort fraction (34.1% CHGA+). Again, further enrichment of CHGA+ cells was observed upon aggregation of the CD318 bound fraction. The CD318 bound aggregates were 93.9% CHGA+ (2.75× enrichment).

TABLE 11

ENRICHMENT OF ENDOCRINE CELLS USING IMMUNO-SELECTION WITH CD200 AND CD318

|  | Pre-sort Endocrine % | Bound Endocrine % | Bound Endocrine Fold Enrichment | Bound Aggregate Endocrine % | Bound Aggregate Endocrine Fold Enrichment |
|---|---|---|---|---|---|
| CD200 | CD200+ CHGA+ = 35.7% | CD200+ CHGA+ = 67.5% | CHGA = 1.89X | CHGA+ = 84.0% | CHGA = 2.35X |
|  | CD200+ INS+ = 8.2% | CD200+ INS+ = 19.9% | INS = 2.43X | INS+ = 22.5% | INS = 2.74X |
| CD200 | CD200+ CHGA+ = 11.4% | CD200+ CHGA+ = 33.2% | CHGA = 2.91X | n.d. | n.d. |
| CD318 | CD318+ CHGA+ = 34.1% | CD318+ CHGA+ = 71.0% | CHGA = 2.08X | CHGA+ = 93.9% | CHGA = 2.75X |

Expression of CD200 on endocrine cells was further characterized by performing immunofluoroscence cytochemistry substantially as described in Example 3 for CD142. Cell surface staining of CD200 on CHGA+ cells was observed in stage 5 differentiated cultures.

In view of the foregoing data, there is a sub-population of hES-derived pancreatic endoderm type cells, in particular, pancreatic epithelium and pancreatic endocrine phenotypes, which are positive for CD142 and CD200, respectively. The CD142 staining pancreatic epithelial cells were co-positive or co-stained with some Pdx1 but not with CHGA+ stained cells, which cells are characteristic of pancreatic endocrine cells at this stage of differentiation. Conversely, CD200 staining pancreatic endocrine cells were co-positive or co-stained with mostly CHGA+ cells but not with PDX1 epithelium stained cells. These data indicate that at least CD142 and CD200 are markers which to date have not been described to enrich, isolate, deplete, separate, sort and/or purify human pancreatic epithelium and pancreatic endocrine phenotype cells. Such marker(s) provide a method for purifying hES-derived cell types for therapeutic applications.

EXAMPLE 7

Pancreatic Endoderm Cell Cultures

Human ES cells were differentiated to late stage 4 early stage 5 and then analyzed by flow cytometry using anti-PDX1-APC(R&D Systems #$IC_{2419}A$), anti-CHGA, and anti-NKX6.1 antibodies as described above. Using this combination of markers the composition of the following cell types in hES-derived cultures can be identified: Pancreatic endoderm (CHGA−PDX1+NKX6.1+), endocrine cells (CHGA+), and PDX1+ endoderm (CHGA−PDX1+NKX6.1−). Because PDX1+ and NKX6.1+ cells are also expressed in some endocrine cells it is necessary to use CHGA to further distinguish between these pancreatic cell lineages (i.e., pancreatic endoderm vs. pancreatic endocrine cells). However, during embryonic development, only the pancreatic endoderm is expected to contain CHGA− PDX1+NKX6.1+ cells.

Figure 2:
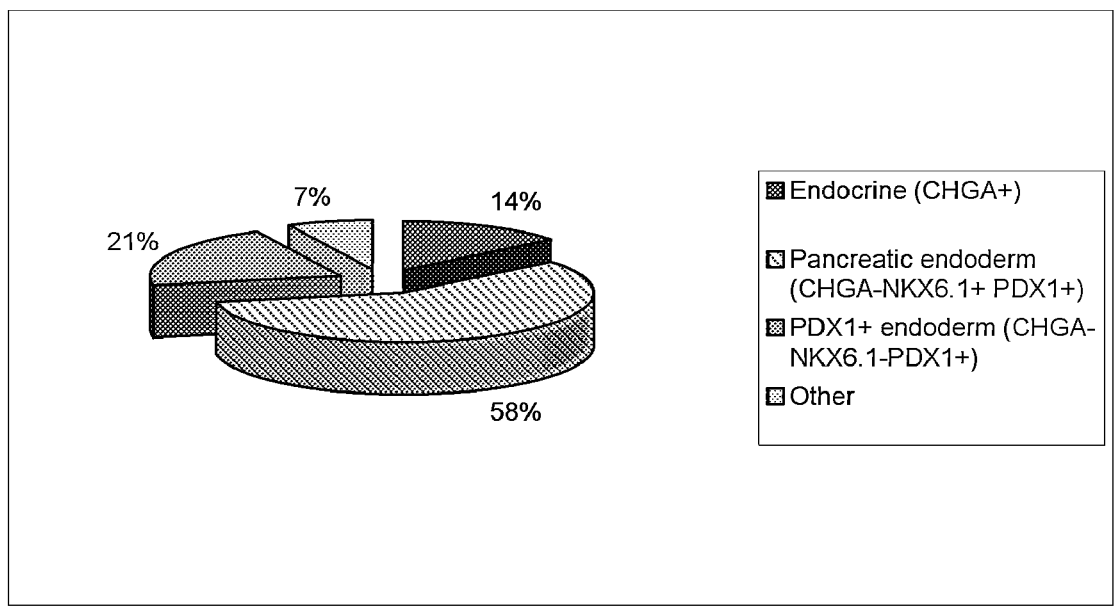
FIG. 2 is a pie chart describing the percentage composition of CHGA+endocrine cells, CHGA−/NKX6.1+/PDX1+ pancreatic endoderm cells, PDX1+ endoderm cells that are CHGA−/NKX6.1− and other cells types in a stage 4/5 cell culture.

As shown in Table 12 and FIG. 2 most of the hES-derived cells in stage 4 to 5 cultures can be identified using the indicated 3 markers. The culture was comprised of 14.08% CHGA+ endocrine cells. As expected some these CHGA+ cells were also positive for PDX1+ and NKX6.1. The culture was also comprised of 57.61% CHGA− PDX1+NKX6.1+ pancreatic endoderm cells and 21.00% CHGA− PDX1+ NKX6.1− cells. Thus, cell cultures enriched in pancreatic endoderm can be obtained. The pancreatic endoderm cells can be further purified using any of the above immuno selection methods described above, e.g., CD142 immuno selection further purifies pancreatic endoderm from other cell populations such as endocrine cells.

TABLE 12

PANCREATIC ENDODERM AND ENDOCRINE CELL TYPES IN STAGE 4-5 HES-DERIVED CULTURES

| Total CHGA− | Pancreatic Endoderm CHGA− NKX6.1+ PDX1+ | CHGA− NKX6.1− PDX1+ | CHGA− NKX6.1+ PDX1− | CHGA− NKX6.1− PDX1− |
|---|---|---|---|---|
| 85.80 | 57.61 | 21.00 | 4.08 | 3.04 |

| Total | CHGA+ NKX6.1+ | CHGA+ NKX6.1− | CHGA+ NKX6.1+ | CHGA+ NKX6.1− |
|---|---|---|---|---|

TABLE 12-continued

PANCREATIC ENDODERM AND ENDOCRINE CELL TYPES IN STAGE 4-5 HES-DERIVED CULTURES

| CHGA+ | PDX1+ | PDX1+ | PDX1− | PDX1− |
|---|---|---|---|---|
| 14.08 | 3.35 | 8.90 | 0.34 | 1.49 |

| Total PDX1+ | Total NKX6.1+ |
|---|---|
| 90.86 | 65.38 |

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications can be made to the invention disclosed herein without departing from the scope and spirit of the invention.

For example, the surface markers discussed herein can be used either alone or in combination with each other, or any of the cell surface markers as described in Table 1 (Example 1). Therefore, anti-CD30, CD49a, CD49e, CD55, CD99, CD165, and CD334 can be used to enrich foregut endoderm. CD55, CD57, CD98, and CD142 can be used to enrich pancreatic endoderm. CD57, CD142, CD200, CD318, and CD340 can be used to enrich endocrine cells. These and other embodiments are encompassed by the present invention.

Also, at least FOXA2 is expressed in definitive endoderm as well as in Stage 2 gut endoderm described herein (Table 2, Example 2), hence the same antibodies which were used to demonstrate immuno-selection (positive and/or negative) can be employed to enrich or purify for definitive endoderm. This same principle can be applied to posterior foregut endoderm (Stage 3), which also expresses PDX1 similar to pancreatic endoderm (Stage 4). Therefore, the antibodies which were used to demonstrate enrichment and purification for pancreatic endoderm can be employed to enrich and purify for posterior foregut.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

What is claimed is:

1. A method of enriching for cells expressing pancreatic and duodenal homeobox gene 1 (PDX1) comprising:
   a) exposing an in vitro cell population comprising PDX1 positive pancreatic cells to a ligand that binds CD142; and
   b) selecting cells that express CD142 thereby enriching for cells expressing PDX1.

2. The method of claim 1, wherein said PDX1 positive cells express NKX6.1.

3. The method of claim 1, wherein the ligand comprises an antibody or binding fragment thereof.

4. The method of claim 1, wherein said ligand is associated with a detectable label.

5. The method of claim 1, wherein said ligand is associated with a magnetic particle.

6. The method of claim 1, wherein said cells are selected by Fluorescence Activated Cell Sorting (FACS).

* * * * *

UNITED STATES PATENT AND TRADEMARK OFFICE
CERTIFICATE OF CORRECTION

| | |
|---|---|
| PATENT NO. | : 8,338,170 B2 |
| APPLICATION NO. | : 12/107020 |
| DATED | : December 25, 2012 |
| INVENTOR(S) | : Olivia Kelly and Anne Bang |

It is certified that error appears in the above-identified patent and that said Letters Patent is hereby corrected as shown below:

Title page, under Other Publications, column 2, line 33
delete "Suupl." and insert --Suppl.--

Title page, under Other Publications, column 2, line 54
delete "beta superfamily" and insert --superfamily--

Title page 2, under Other Publications, column 2, line 10
delete "Phosphtidylinositol" and insert --Phosphatidylinositol--

In the Specification

Column 3, paragraph 41, line 3
insert --.-- after "population"

Column 10, line 37
delete "TGFbeta" and insert --TGF-beta--

Column 14, line 32
delete "allophycocyanin B." and insert --allophycocyanin B,--

Column 16, line 16
delete "GHIRL" and insert --GHRL--

Column 17, line 12
delete "PDX11/NKX6.1" and insert --PDX1/NKX6.1--

Column 17, line 48
delete "HESC" and insert --hESC--

Signed and Sealed this
Twenty-fourth Day of December, 2013

Margaret A. Focarino
*Commissioner for Patents of the United States Patent and Trademark Office*

CERTIFICATE OF CORRECTION (continued)
U.S. Pat. No. 8,338,170 B2

Column 20, line 22
delete "though" and insert --through--

Column 20, line 23
delete "(Hs00182599 ml)," and insert --(Hs00182599_m1),--

Column 20, line 23
delete "(Hs00169795 ml)," and insert --(Hs00169795_m1),--

Column 20, line 24
delete "(Hs00604567 ml)," and insert --(Hs00169795_m1),--

Column 20, line 26
delete "(Hs00154441 ml)." and insert --(Hs00154441_m1).--

Column 21, line 64
delete "thereof," and insert --thereof;--

Column 23, line 33
delete "Fluorochro" and insert --Fluorochrome--

Column 23, line 44
delete "sufhydryl" and insert --sulfhydryl--

Column 24, line 35
delete "Nos." and insert --No.--

Column 24, line 35
delete "O," and insert --O.--

Column 24, line 36
delete "O," and insert --O.--

Column 31, lines 58-59
delete "stretopmycin," and insert --streptomycin,--

Column 31, line 67
delete "cyclopmaine" and insert --cyclopamine--

Column 32, line 19
delete "ng/nL" and insert --ng/mL--

Column 32, line 22
delete "stretopmycin," and insert --streptomycin,--

CERTIFICATE OF CORRECTION (continued)
U.S. Pat. No. 8,338,170 B2

Column 34, line 26
delete "CD30+" and insert --CD30– --

Column 36, line 14
insert --.-- after "6"

Column 37, line 48
delete "HESC" and insert --hESC--

Column 38, line 1
delete "PB S" and insert --PBS--

Column 38, line 23
delete "PB S" and insert --PBS--

Column 41, line 37
delete "PHARMIGEN™" and insert --PHARMINGEN™--

Column 43, line 4
delete "Incease" and insert --Increase--

Column 44, line 51
delete "immunofluoroscence" and insert --immunofluorescence--

Column 45, line 12
delete "#IC$_{2419}$A)," and insert --#IC2419A),--